(12) United States Patent
Dunaway et al.

(10) Patent No.: US 10,246,700 B2
(45) Date of Patent: Apr. 2, 2019

(54) METHODS AND APPARATUSES FOR GENE PURIFICATION AND IMAGING

(71) Applicant: NanoString Technologies, Inc., Seattle, WA (US)

(72) Inventors: Dwayne Dunaway, Seattle, WA (US); Rustem Khafizov, Seattle, WA (US); Qian Mei, Seattle, WA (US); Lucas Dennis, Edmonds, WA (US); Michael Krouse, Seattle, WA (US); Joseph M. Beechem, Eugene, OR (US); Isaac Sprague, Seattle, WA (US)

(73) Assignee: NanoString Technologies, Inc., Seattle, WA (US)

( * ) Notice: Subject to any disclaimer, the term of this patent is extended or adjusted under 35 U.S.C. 154(b) by 264 days.

(21) Appl. No.: 14/948,776

(22) Filed: Nov. 23, 2015

(65) Prior Publication Data

US 2016/0145602 A1    May 26, 2016

Related U.S. Application Data

(60) Provisional application No. 62/083,681, filed on Nov. 24, 2014.

(51) Int. Cl.
| | | |
|---|---|---|
| *C12Q 1/68* | (2018.01) | |
| *C12N 15/10* | (2006.01) | |
| *C12Q 1/6837* | (2018.01) | |
| *C12Q 1/6825* | (2018.01) | |
| *B01L 3/00* | (2006.01) | |
| *C12Q 1/6816* | (2018.01) | |

(52) U.S. Cl.
CPC .... *C12N 15/1013* (2013.01); *B01L 3/502723* (2013.01); *B01L 3/502761* (2013.01); *C12Q 1/6816* (2013.01); *C12Q 1/6825* (2013.01); *C12Q 1/6837* (2013.01); *B01L 3/502715* (2013.01); *B01L 2200/0631* (2013.01); *B01L 2200/0668* (2013.01); *B01L 2200/10* (2013.01); *B01L 2300/0627* (2013.01); *B01L 2300/0867* (2013.01); *B01L 2300/0887* (2013.01); *B01L 2300/1827* (2013.01); *B01L 2400/043* (2013.01); *B01L 2400/0487* (2013.01)

(58) Field of Classification Search
CPC .. C12Q 1/6816; C12Q 1/6825; C12Q 1/6837; C12Q 2525/161; C12Q 2563/155; B01L 2200/0631; B01L 2200/0668; B01L 2200/10; B01L 2300/0627; B01L 2300/0867; B01L 2300/1827; B01L 3/502723; B01L 3/502761; B01L 2300/0887; B01L 2400/043; B01L 2400/0487; B01L 3/502715; C12N 15/1013
USPC .......................... 435/283.1, 91.2, 6
See application file for complete search history.

(56) References Cited

U.S. PATENT DOCUMENTS

| | | | |
|---|---|---|---|
| 7,473,767 B2 | 1/2009 | Dimitrov | |
| 7,919,237 B2 | 4/2011 | Dimitrov et al. | |
| 7,941,279 B2 | 5/2011 | Hwang et al. | |
| 8,148,512 B2 | 4/2012 | Dimitrov | |
| 8,415,102 B2 | 4/2013 | Geiss et al. | |
| 8,492,094 B2 | 7/2013 | Dimitrov et al. | |
| 8,519,115 B2 | 8/2013 | Webster et al. | |
| 8,986,926 B2 | 3/2015 | Ferree | |
| 9,066,963 B2 | 6/2015 | Perou et al. | |
| 9,181,588 B2 | 12/2015 | Perou et al. | |
| 2011/0086774 A1 | 4/2011 | Dunaway | |
| 2011/0145176 A1 | 6/2011 | Perou et al. | |
| 2011/0201515 A1 | 8/2011 | Webster et al. | |
| 2011/0229888 A1 | 9/2011 | Hengen et al. | |
| 2012/0329142 A1* | 12/2012 | Battrell | B01F 11/0071 435/287.2 |
| 2013/0004482 A1 | 1/2013 | Perou et al. | |
| 2013/0017971 A1 | 1/2013 | Geiss et al. | |
| 2013/0178372 A1 | 7/2013 | Geiss et al. | |
| 2013/0230851 A1 | 9/2013 | Geiss et al. | |
| 2013/0337444 A1 | 12/2013 | Ferree et al. | |
| 2013/0345161 A1 | 12/2013 | Perou et al. | |
| 2014/0005067 A1 | 1/2014 | Webster et al. | |
| 2014/0017688 A1 | 1/2014 | Webster et al. | |

(Continued)

FOREIGN PATENT DOCUMENTS

| | | |
|---|---|---|
| EP | 1990638 A1 | 11/2008 |
| WO | WO 2012/178046 A2 | 12/2012 |
| WO | WO 2013/082440 A2 | 6/2013 |

OTHER PUBLICATIONS

International Search Report issued by the International Search Authority dated Mar. 11, 2016, in connection with corresponding international patent application No. PCT/US2015/062109.

(Continued)

*Primary Examiner* — Cynthia B Wilder
(74) *Attorney, Agent, or Firm* — Cooley LLP; Ivor R. Elrifi; Matthew Pavao

(57) ABSTRACT

The present disclosure is directed to systems, devices and methods for nucleic acid or protein purification and imaging. A system is provided including a cartridge comprising a sample input area configured to hold a sample, comprising a plurality of hybridized complexes comprising a plurality of target molecules each hybridized with probes and a plurality of non-hybridized probes. The cartridge may also include a first binding chamber configured with first magnetic beads to receive and bind the sample, a first elution channel configured to receive the first magnetic beads and elute the sample from the first magnetic beads, a second binding chamber configured with second magnetic beads to receive and bind the sample, a second elution channel configured to receive the second magnetic beads and elute the sample from the second magnetic beads, and a binding area configured to receive the eluted sample and hold molecules for imaging.

21 Claims, 39 Drawing Sheets
(37 of 39 Drawing Sheet(s) Filed in Color)

Specification includes a Sequence Listing.

(56) References Cited

U.S. PATENT DOCUMENTS

| | | |
|---|---|---|
| 2014/0037620 A1 | 2/2014 | Ferree et al. |
| 2014/0087959 A1 | 3/2014 | Ellis et al. |
| 2014/0154681 A1 | 6/2014 | Wallden |
| 2014/0162251 A1 | 6/2014 | Dimitrov |
| 2014/0200167 A1* | 7/2014 | Prakash .................. B01L 3/567 506/39 |
| 2014/0371088 A1 | 12/2014 | Webster |
| 2015/0072021 A1 | 3/2015 | Cheang et al. |
| 2015/0252440 A1 | 9/2015 | Perou et al. |

OTHER PUBLICATIONS

Kulkarni "Digital Multiplexed Gene Expression Analysis Using the NanoString nCounter System," *Current Protocols in Molecular Biology*, 25B.10.1-25B.10.17, Apr. 2011.

* cited by examiner

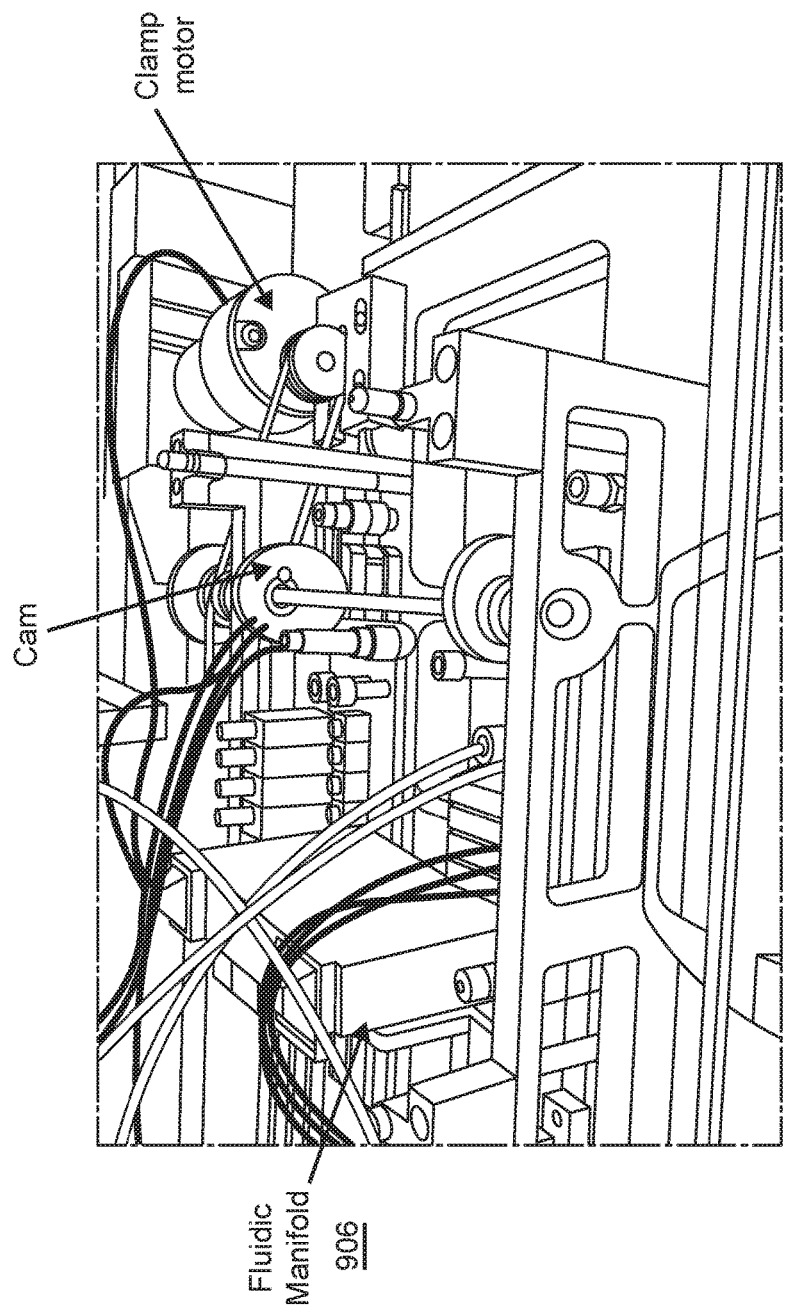

1302

1502

1504

1602

1604

SEQUENCE LISTING

```
<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 1
gctgtgatga tagac                                                  15

<210> SEQ ID NO 2
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 2
ggtctgtgtg atgtt                                                  15
```

METHODS AND APPARATUSES FOR GENE PURIFICATION AND IMAGING

CROSS-REFERENCE TO RELATED APPLICATIONS

This Application claims priority under 35 U.S.C. § 119 to U.S. Provisional Application Ser. No. 62/083,681, filed Nov. 24, 2014. The contents of the aforementioned application are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Nov. 23, 2015, is named NATE-023_ST25.txt and is 815 bytes in size.

FIELD OF THE INVENTION

The present innovations generally address molecular sample digital counting, and more particularly, include methods and apparatuses for nucleic acid and protein sample purification and imaging of associated molecular barcodes.

However, in order to develop a reader's understanding of the innovations, disclosures have been compiled into a single description to illustrate and clarify how aspects of these innovations operate independently, interoperate as between individual innovations, and/or cooperate collectively. The application goes on to further describe the interrelations and synergies as between the various innovations; all of which is to further compliance with 35 U.S.C. § 112.

BACKGROUND OF THE INVENTION

Scientists use a plurality of methods to purify and detect molecules. Conventional systems have fluidics and imaging of molecular barcodes in separate instruments, have one illumination channel per emission channel, and have inefficient methods of moving the sample through the purification and imaging machine.

SUMMARY OF THE INVENTION

The present invention provides systems, devices and methods for nucleic acid or protein purification and imaging.

An aspect of the present invention provides a cartridge configured for purifying a hybridized target molecule sample and imaging the hybridized target molecule. The cartridge comprises a sample input area, a first binding chamber, a first elution channel, a second binding chamber, a second elution channel, and a binding area.

In this aspect, the sample input area may be configured to hold a target molecule sample, e.g., comprising a plurality of hybridized complexes (which include a plurality of target molecules each hybridized with a first probe and/or a second probe), a plurality of non-hybridized first probes, and a plurality of non-hybridized second probes. The first binding chamber may be configured to receive and/or contain a first affinity matrix and/or to receive the sample. The first affinity matrix may be functionalized with first molecules configured to bind with the non-hybridized first probes and/or hybridized complexes of the sample during a first period of time. The first binding chamber may be additionally configured to receive a first buffer to remove non-hybridized second probes from the sample after the non-hybridized first probes and/or hybridized complexes of the sample bind with the first affinity matrix. The first elution channel may be configured to receive the first affinity matrix after the first period of time and/or configured for heating the first affinity matrix to elute a first eluted sample comprising the plurality of hybridized complexes and/or plurality of non-hybridized first probes. The second binding chamber may be configured to receive and/or contain a second affinity matrix and/or to receive the first eluted sample. The second affinity matrix may be functionalized with second molecules configured to bind with the hybridized complexes during a second period of time. The second binding chamber may be additionally configured to receive a second buffer to remove at least non-hybridized first probes. The second elution channel may be configured to receive the second affinity matrix after the second period of time and/or configured for heating the second affinity matrix to elute a second eluted sample comprising the plurality of hybridized complexes. The binding area may have an active binding surface configured to receive the second eluted sample and/or bind with the hybridized complexes.

In embodiments of this aspect, the target molecule may be a nucleic acid or a protein. In embodiments, the first affinity matrix and/or the second affinity matrix, respectively, correspond to a first set of magnetic beads (e.g., oligonucleotide-coupled magnetic beads, e.g., F magnetic beads) and/or a second set of magnetic beads (e.g., oligonucleotide-coupled magnetic beads, e.g., G magnetic beads). The cartridge may further comprise a plurality of buffer input areas, a plurality of first binding chambers, a plurality of waste output areas, and/or a plurality of bead pads. The bubble vent may be configured to separate the sample input and/or the first binding chamber and/or to eliminate air bubbles. In embodiments, the active binding surface may comprise streptavidin, an avidin (e.g., Neutravidin™), or oligonucleotides. In embodiments, the first probes include capture probes. In embodiments, the second probes include reporter probes. In embodiments, the cartridge may be operatively coupled to a plurality of off-card buffer input valves operatively coupled to a fluidic manifold and/or a plurality of waste valves. In embodiments, the cartridge further comprises a plurality of on-card buffer input valves operatively coupled to a fluidic manifold. The plurality of off-card buffer input valves may be configured to receive the first buffer and/or the second buffer from the fluidic manifold and/or provide the buffer to the cartridge. In embodiments, the flow of the second eluted sample onto the binding area may be done in small steps that may be re-ordered based on pressure profiles. In embodiments, the binding area may be further configured to receive a solution (e.g., comprising includes G-hooks, anti-fade media, and/or fiducials) formulated to immobilize the second eluted sample on the active binding surface after stretching with flow.

Another aspect of the present invention provides a cartridge configured for purifying a hybridized target molecule sample and imaging the hybridized target molecule. The cartridge comprises a buffer input area, a bubble vent, a first binding chamber, a first elution channel, a second binding chamber, a second elution channel, and a binding area.

In this aspect, the buffer input area may be configured to hold a target molecule sample, e.g., comprising a plurality of hybridized complexes (which include a plurality of target molecules, reporter probes, and/or capture probes), a plurality of non-hybridized reporter probes, and/or a plurality of non-hybridized capture probes. The bubble vent may be configured to separate the sample input and the first binding chamber and/or to eliminate air bubbles. The first binding chamber may be configured to receive and/or contain F magnetic beads and/or to receive the sample. The first binding chamber may be additionally configured to receive a first buffer to remove non-hybridized reporter probes from the sample after the non-hybridized reporter probes and/or hybridized complexes of the sample bind with the F magnetic beads, which may be functionalized with first molecules configured to bind with the non-hybridized reporter probes and/or hybridized complexes of the sample during a first period of time. The first elution channel may be configured to receive the F magnetic beads after the first period of time and/or configured for heating the F magnetic beads to elute a first eluted sample comprising the plurality of hybridized complexes and/or plurality of non-hybridized reporter probes. The second binding chamber may be configured to receive and/or contain G magnetic beads and/or to receive the first eluted sample. The second binding chamber may be additionally configured to receive a second buffer to remove at least non-hybridized capture probes. The G magnetic beads may be functionalized with second molecules configured to bind with the hybridized complexes during a second period of time. The second elution channel may be configured to receive the G magnetic beads after the second period of time and/or configured for heating the G magnetic beads to elute a second eluted sample comprising the plurality of hybridized complexes. The binding area may have an active binding surface configured to receive the second eluted sample and/or bind with the hybridized complexes. The cartridge may be operatively coupled to a plurality of off-card buffer input valves operatively coupled to a fluidic manifold. The plurality of off-card buffer input valves may be configured to receive the first buffer and/or the second buffer from the fluidic manifold and/or provide the first and/or buffer to the cartridge. The plurality of waste valves may be configured to collect the first and/or second buffer from the cartridge.

In embodiments of this aspect, the target molecule may be a nucleic acid or a protein. In embodiments, the active binding surface may comprise streptavidin, an avidin (e.g., Neutravidin™), or oligonucleotides.

Yet another aspect of the present invention provides a system for imaging a plurality of hybridized complexes. The system comprises a cartridge of any of the herein described aspects or embodiments, a cartridge tray operatively coupled to the system and configured to hold the cartridge, a first heater operatively coupled to the cartridge, a second heater operatively coupled to the cartridge, a magnet operatively coupled to the imaging device below the cartridge tray, a fluidic manifold operatively coupled to the system above the cartridge tray and configured to hold and/or control the flow of a plurality of buffers, a plurality of off-card buffer input valves operatively coupled to the fluidic manifold and the cartridge; a plurality of waste valves operatively coupled to the system above the cartridge tray, and an imaging reference surface operatively coupled to the imaging device above the cartridge tray.

In embodiments of this aspect, the first heater may be configured to heat the first elution channel. In embodiments, the second heater may be configured to heat the second elution channel. In embodiments, the magnet may be configured to move the first magnetic beads and/or the second magnetic beads within the first and/or second binding chambers and/or the first and/or second elution channels. In embodiments, the magnet may be configured to move parallel to the cartridge tray. In embodiments, the plurality of off-card buffer input valves may be configured to receive the plurality of buffers from the fluidic manifold and/or provide the plurality of buffers to the cartridge. In embodiments, the plurality of waste valves may be configured to collect the plurality of buffers from the cartridge. In embodiments, the system further comprises a cam contact pad operatively coupled to the imaging device and configured to allow preloading against at least one contact pad, at least one adjustable contact between a moving clamp and a base of the imaging device, the at least one adjustable contact configured to allow for datum A adjustment, and a clamp motor operatively coupled to the imaging device and configured to move the moving clamp. In embodiments, at least one of the plurality of off-card buffer input valves and the plurality of waste valves operatively coupled to the system above the cartridge tray may be pneumatically controlled.

Another aspect of the present invention provides a method for purifying a hybridized target molecule sample and imaging the hybridized target molecule. The method comprises steps of:
  (a) receiving a hybridized sample, the sample comprising a plurality of hybridized, complexes comprising target molecules hybridized with first probes and second probes, a plurality of non-hybridized first probes, and a plurality of non-hybridized second probes
  (b) binding the non-hybridized first probes and hybridized complexes of the sample to a first affinity matrix during a first period of time to produce a first mixture,
  (c) flowing a first buffer through the first mixture to remove non-hybridized second probes from the first mixture after the non-hybridized first probes and hybridized complexes of the sample bind with the first affinity matrix,
  (d) heating the first mixture to free the non-hybridized first probes and hybridized complexes from the first affinity matrix and elute a first eluted sample comprising the plurality of hybridized complexes and plurality of non-hybridized first probes,
  (e) binding the hybridized complexes of the first eluted sample to a second affinity matrix during a second period of time to produce a second mixture,
  (f) flowing a second buffer through the second mixture to remove the non-hybridized first probes from the first eluted sample after the hybridized complexes bind with the second affinity matrix,
  (g) heating the second mixture to free the hybridized complexes from the second affinity matrix to elute a second eluted sample comprising the plurality of hybridized complexes, and
  (h) binding the hybridized complexes to an active binding surface for imaging thereof.

In embodiments of this aspect, the target molecule may be a nucleic acid or a protein. In embodiments, the first affinity matrix and the second affinity matrix, respectively, correspond to a first set of magnetic beads and a second set of magnetic beads, respectively. In embodiments, the active binding surface may surface may comprise streptavidin, an avidin (e.g., Neutravidin™), or oligonucleotides.

A further aspect of the present invention provides a method for purifying a hybridized target molecule sample and imaging the hybridized target molecule. The method comprising steps of:
  (a) providing the cartridge of any of the herein described aspects or embodiments,
  (b) receiving a hybridized sample, the sample comprising a plurality of hybridized complexes comprising target molecules hybridized with first probes and second probes, a plurality of non-hybridized first probes, and a plurality of non-hybridized second probes, (c) binding the non-hybridized first probes and hybridized complexes of the sample to a first affinity matrix in a first binding chamber during a first period of time, (d) flowing a first buffer into the first binding chamber to remove non-hybridized second probes from the sample after the non-hybridized first probes and hybridized complexes of the sample bind with the first affinity matrix, (e) directing the first affinity matrix into a first elution channel, (f) heating the first affinity matrix to elute a first eluted sample comprising the plurality of hybridized complexes and plurality of non-hybridized first probes, (g) binding the hybridized complexes of the first eluted sample to a second affinity matrix in a second binding chamber during a second period of time, (h) flowing a second buffer into the second binding chamber to remove the non-hybridized first probes from the first eluted sample after the hybridized complexes bind with the second affinity matrix, (i) heating the second affinity matrix to elute a second eluted sample comprising the plurality of hybridized complexes, and (j) binding the hybridized complexes to an active binding surface for imaging thereof.

In embodiments of this aspect, the target molecule may be a nucleic acid or a protein. In embodiments, the first affinity matrix and the second affinity matrix, respectively, correspond to a first set of magnetic beads (e.g., F magnetic beads) and a second set of magnetic beads (e.g., G magnetic beads). In embodiments, the active binding surface may surface may comprise streptavidin, an avidin (e.g., Neutravidin™), or oligonucleotides. In embodiments, the first probes include reporter probes. In embodiments, the second probes include capture probes. In embodiments, the first binding chamber may be an F binding chamber. In embodiments, the first period of time may be a period of about 8 minutes. In embodiments, the first magnetic beads may be heated to about 47° C. for about 7 minutes. In embodiments, the second binding chamber may be a G binding chamber. In embodiments, the second buffer may be F-elution fluid. In embodiments, the second period of time may be a period of about 7 minutes. In embodiments, the second buffer may be added to the second binding chamber in increments of 2µforward and 1 µL backward. In embodiments, the second buffer may be added in increments of about +2.8 µL, +2 µL, −1 µL, +2 µL, −1 µL, +1.5 µL, and 7 µL. In embodiments, the second magnetic beads may be heated to about 47° C. for about 7 minutes. In embodiments, the method further comprises a step of moving a quantity of the first eluted sample across an affinity matrix pad in a first direction and a second direction. In embodiments, the first buffer may be pumped to move sample-bead mixture through the first bead pad in a first direction and a second direction. In embodiments, the first buffer may be added in increments of approximately +15 µL, and −15 µL. Any of the above aspects and embodiments can be combined with any other aspect or embodiment.

Unless otherwise defined, all technical and scientific terms used herein have the same meaning as commonly understood by one of ordinary skill in the art to which this invention belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present invention, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the invention will be apparent from the following detailed description and claim.

BRIEF DESCRIPTION OF THE DRAWINGS

The patent or application file contains at least one drawing executed in color. Copies of this patent or patent application publication with color drawings will be provided by the Office upon request and payment of the necessary fee.

The accompanying appendices and/or drawings illustrate various non-limiting, example, innovative aspects in accordance with the present descriptions.

The leading number of each reference number within the drawings indicates the figure in which that reference number is introduced and/or detailed. As such, a detailed discussion of reference number 101 would be found and/or introduced in FIG. 1. Reference number 201 is introduced in FIG. 2, etc.

DETAILED DESCRIPTION

Before some embodiments of the present disclosure are described in detail, it is to be understood that such embodiments are not limited to particular variations set forth and may, of course, vary. Various changes may be made to embodiments described and equivalents may be substituted without departing from the true spirit and scope of inventions disclosed herein. In addition, many modifications may be made to adapt a particular situation, material, composition of matter, process, process act(s) or step(s), to the objective(s), spirit or scope of the present disclosure. All such modifications are intended to be within the scope of any and all claims supported by the present disclosure.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within embodiments of the disclosure. Also, it is contemplated that any optional feature of one and/or another of the disclosed embodiments described herein may be set forth and claimed independently, or in combination with any one or more of the features described herein.

Reference to a singular item, includes the possibility that there are plural of the same items present. More specifically, as used herein and in the appended claims, the singular forms "a," "and," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

In some embodiments, a user reading a sample (e.g., a nucleic acid sample) may wish to use a single device to both purify and detect the sample. In some embodiments, using a single device for both purposes may reduce processing time, likelihood of contamination, cost of performing imaging analysis, reduce the overall system cost, reduce hands on time/steps, and/or the like.

Figure 1A:
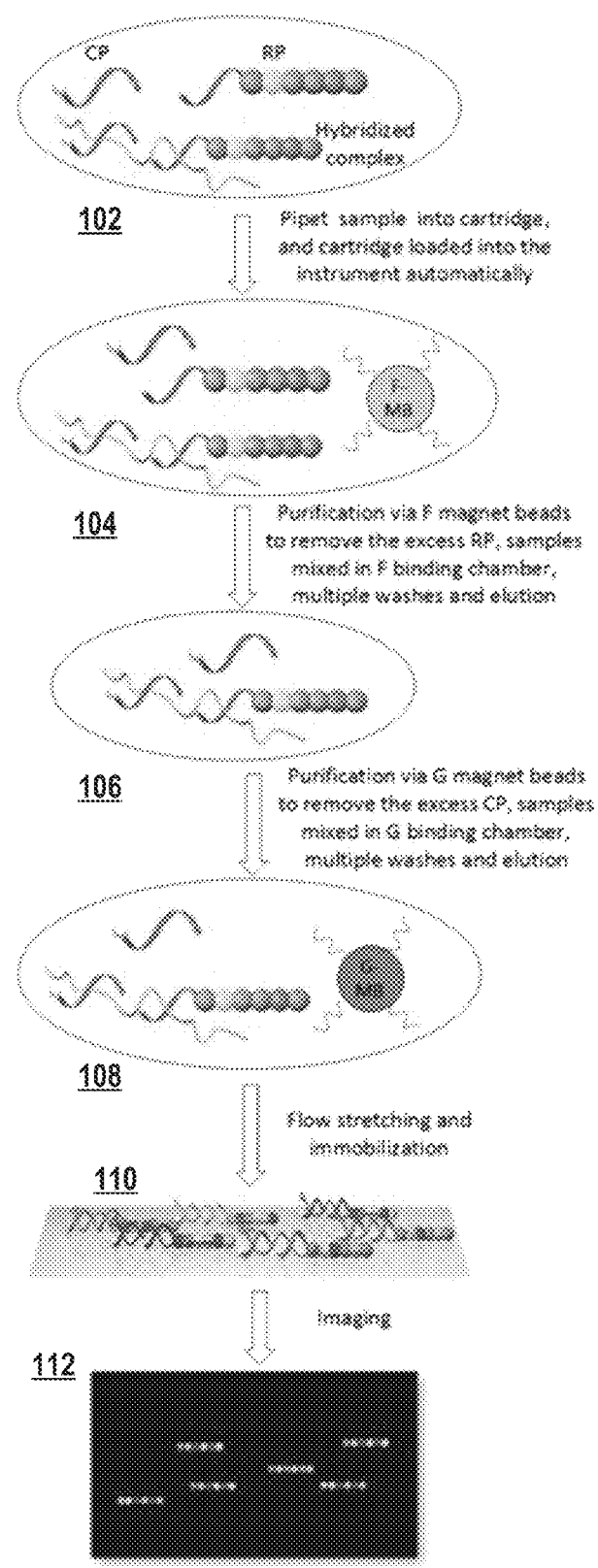
FIG. 1A shows block diagrams of the major processes according to some embodiments.
Figure 1B:
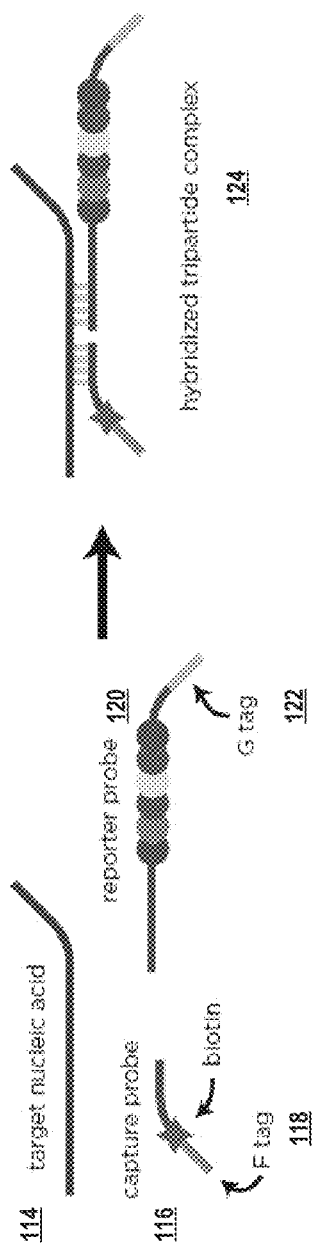
FIGS. 1B-E show block diagrams illustrating the basic underlying chemistry according to some embodiments.

FIGS. 1A-E show block diagrams illustrating a purification and imaging process according to some embodiments. For example, a user of the instrument may hybridize and/or otherwise prepare a sample for processing. Referring to FIG. 1B, in some examples, the user may wish to hybridize a target nucleic acid 114, e.g., using probes configured to bind to the target nucleic acid 114, and including affinity tags configured to bind to magnetic beads. Target nucleic acids 114 may include all forms of nucleic acids (e.g., RNA, DNA, microRNA, and/or the like). Proteins, and/or any other molecules which can be attached to the capture and/or reporter probes (e.g., which may be detected through a nucleic acid intermediate) may also be hybridized for analysis. For example, hybridization may involve mixing target nucleic acids with capture probes 116 and reporter probes 120. A capture probe 116 may include a biotin moiety used to bind the complex to an imaging surface, and/or an F tag configured to bind to F magnetic beads. A reporter probe 120 may include a fluorescent barcode used in the imaging process, and/or a G tag configured to bind to G magnetic beads. When the target nucleic acid 114 binds to a reporter and capture probe, it may create a hybridized tripartite complex 124 which may then be purified for imaging and/or like processes.

Figure 9A:
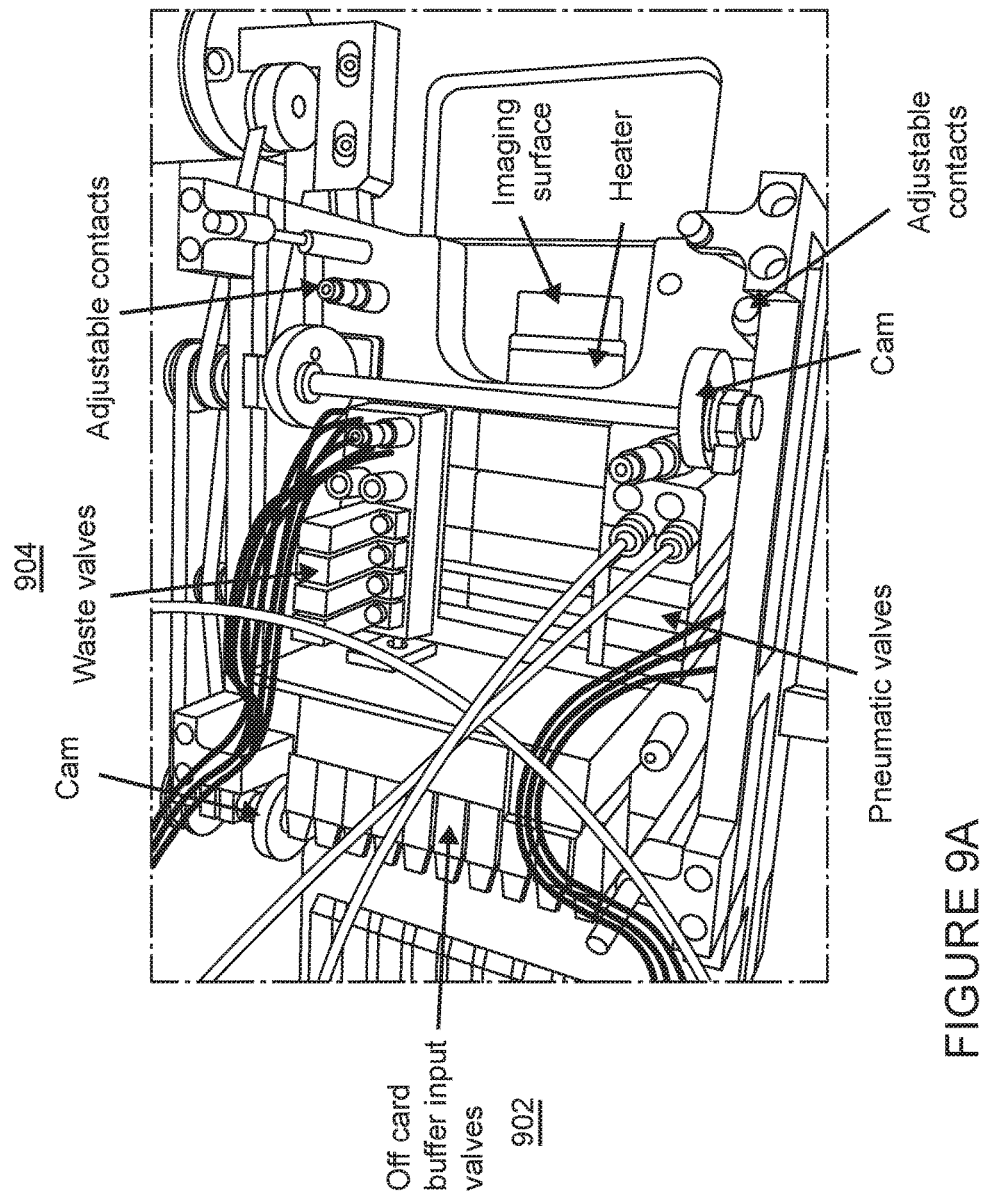

As shown in FIG. 1B, two approximately 50 base pair probes hybridize directly to each target molecule in solution to form a hybridized tripartite complex. The reporter probe carries a specific fluorescent barcode, and the capture probe contains a biotin moiety that later binds the tripartite complex to the imaging surface. Both probes contain affinity tags (called "F" or "G") that are required for magnetic bead-based purification and immobilization Referring to FIG. 1A, the user may pipet 102 a sample (e.g., a hybridized nucleic acid sample and/or a like hybridized biological sample) into a sample cartridge configured to be placed in a cartridge tray of the instrument (which may be handled automatically via aspects/embodiments of the present disclosure). The hybridized biological sample may also include non-hybridized probes which may not have bound to the genes (e.g., excess probes). The cartridge may also have pads (e.g., glass fiber pads) configured to hold magnetic beads. Magnetic beads can be of a plurality of varieties, such as F beads, G beads, and/or the like. In some implementations, F beads are magnetic beads coupled to DNA oligonucleotides which are the reverse complement of repeated sequences found on the capture probe, and are used as an affinity matrix to separate hybridized complexes and free capture and/or reporter probes during purification. The magnetic beads may be dried down with buffer and a sugar (e.g., trehalose) to stabilize the beads and to prepare them for suspension in a sample. The cartridge may also be configured with on-card buffer input valves configured to receive buffer from off-card buffer valves (e.g., see 902 of FIG. 9A), and pneumatic valves configured to control flow between binding chambers, elution chambers, and/or like areas used for purification processes and waste containers configured to hold used elution fluids.

Figure 4:
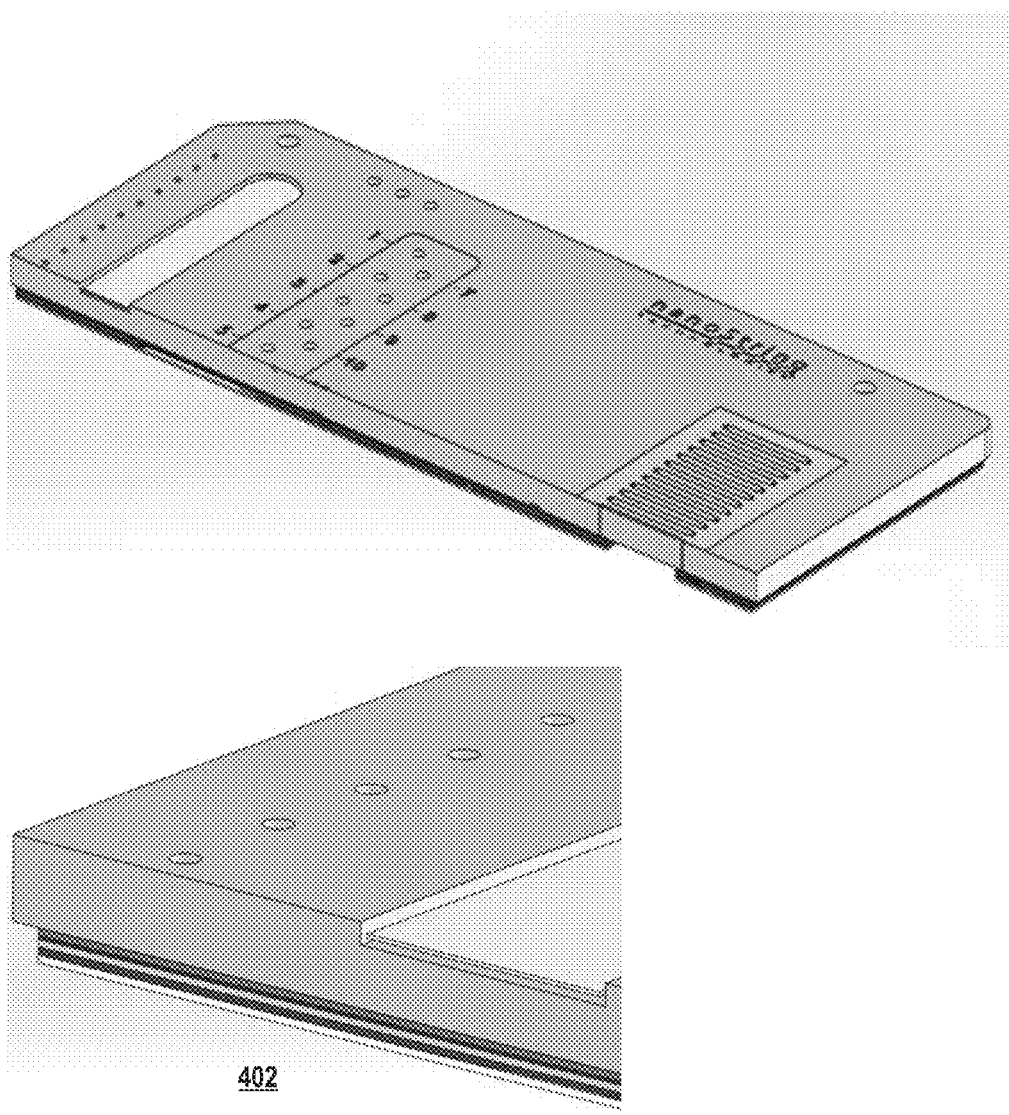
FIG. 4 shows a pictorial diagram illustrating the layer stack-up to build the cartridge according to some embodiments.

The cartridge may be a multi-layer cartridge (e.g., see 402 in FIG. 4) comprising the following components:

| Layers | Materials | Color |
|---|---|---|
| 1 | 250 μm Melinex ® | white |
| 2 | 250 μm ACA | Blue |
| 3 | 250 μm PDMS | Yellow |
| 4 | 120 μm PDMS | Red |
| 5 | 250 μm ACA | green |
| 6 | 3 mm PMMA | grey |

Figure 3A:
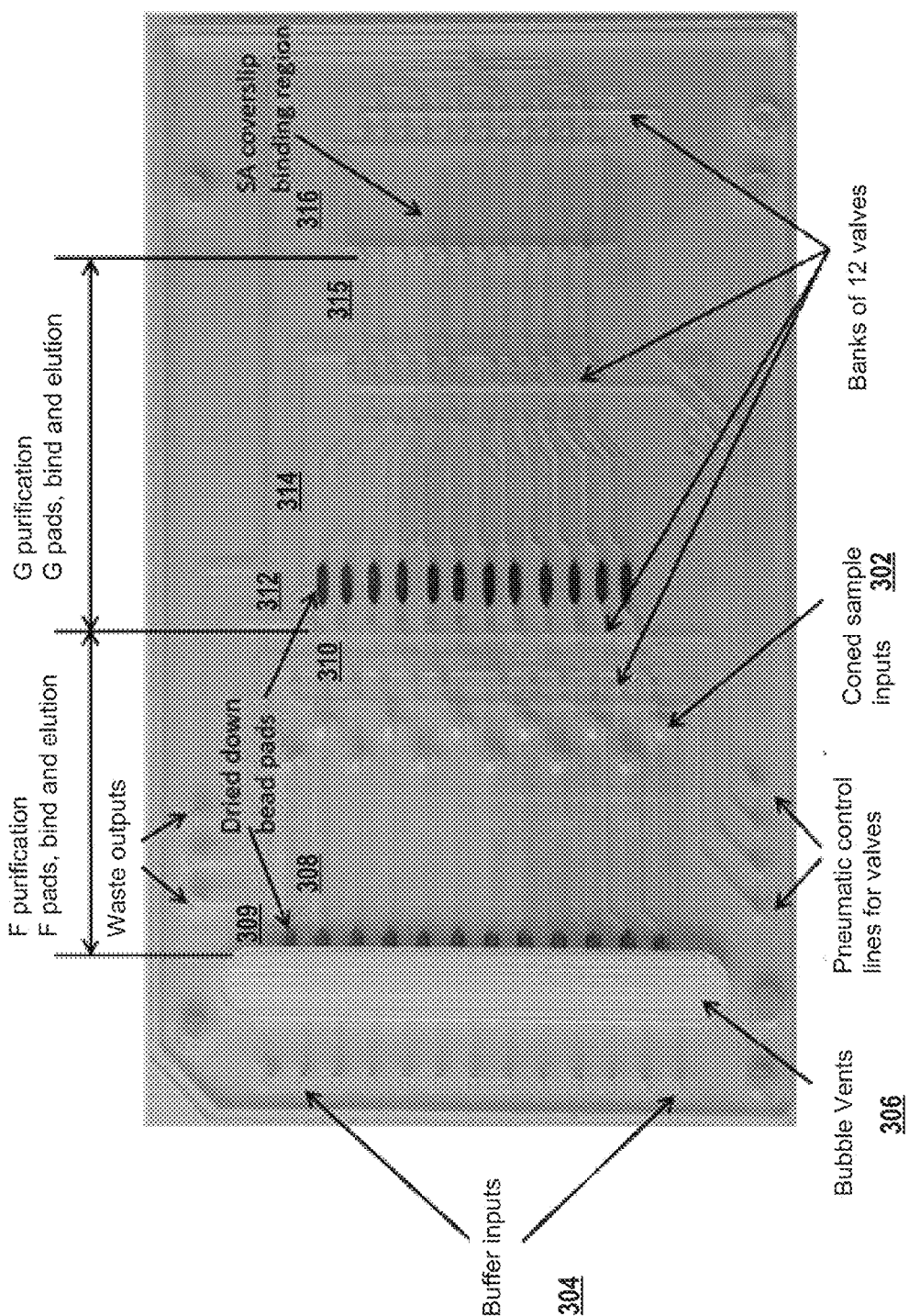
FIG. 3A shows a labeled picture of the fluidic cartridge.
Figure 3B:
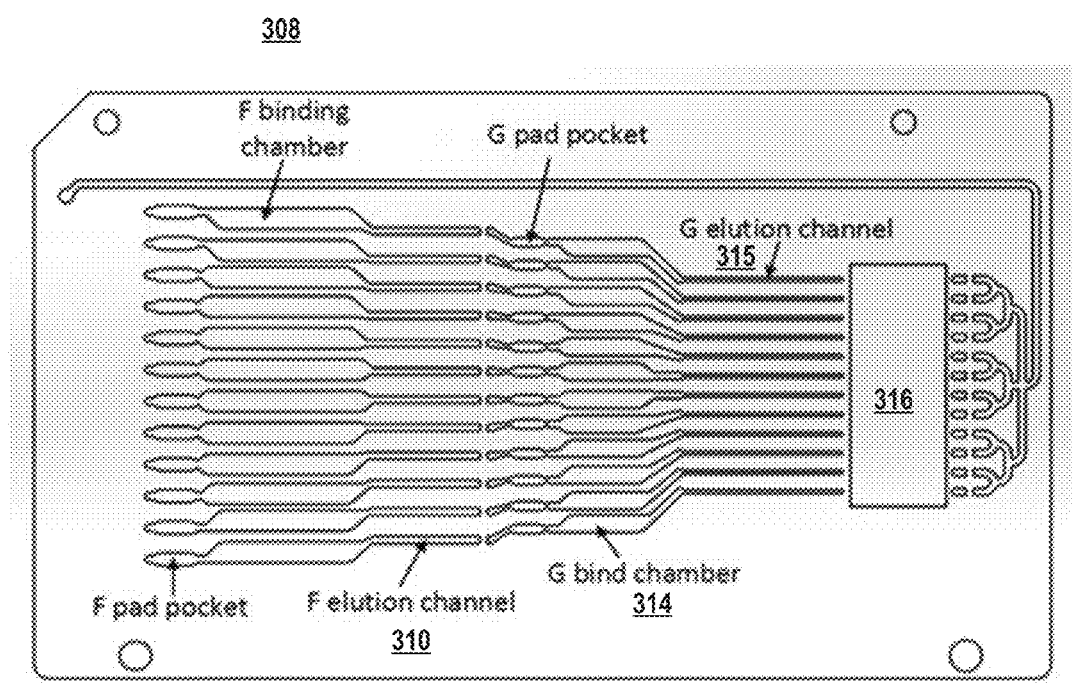
FIG. 3B shows the fluidic layer where the two purifications occur.

Referring to FIG. 1A, the sample may be introduced to dry magnetic beads (e.g. F magnetic beads (e.g., F beads, anti-F magnetic beads) which are coupled to a 15-mer DNA oligonucleotide, 5'-GCT GTG ATG ATA GAC-3' (SEQ ID NO: 1), complementary to the repeats on the capture probe) configured to remove excess of at least one type of probe (e.g., the reporter probes) from the hybridized sample (e.g., see 104 of FIG. 1A). The F beads may be dried down in 5× SSPE and 40% trehalose on pads (e.g., see 309 of FIG. 3A; bead pad is partially hidden under bubble vent). In some embodiments, the F beads and the sample may be combined in a binding chamber (e.g., see 308 of FIGS. 3A & 3B) configured to facilitate the binding of the F beads to the hybridized tripartite complex molecules (e.g., see 126 of FIG. 1C), and to allow for the beads to be washed such that at least some of the unhybridized probes (e.g., reporter probes) are washed from the sample (e.g., see 128 of FIG. 1C). The binding chamber may be configured with an elution channel (e.g., see 310 of FIGS. 3A & 3B) which may allow for the beads be heated (e.g., to 47° C.) and the sample to be eluted (e.g., see 130 of FIG. 1C).

Figure 1C:
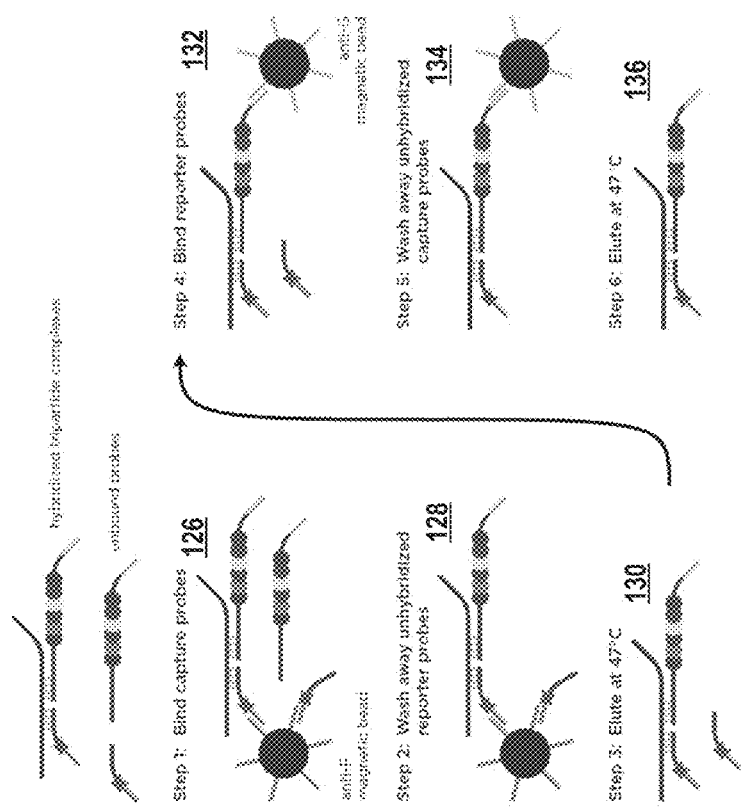

The sample may then be passed to a second magnetic bead binding chamber (e.g., see 106 of FIG. 1A & 314 of FIGS. 3A & 3B) which may be configured to hold another set of magnetic beads (e.g., G magnetic beads, also known as G beads and/or anti-G magnetic beads, which are coupled to a 15-mer DNA oligonucleotide, 5'-GGT CTG TGT GAT GTT-3' (SEQ ID NO: 2), complementary to the repeats on the reporter probe) which may be able to bind to the reporter probes of the hybridized tripartite complex molecules (e.g., see 132 of FIG. 1C). The second magnetic bead binding chamber (e.g., see 314 of FIGS. 3A & 3B) may also allow for washing the sample to remove excess molecules of another type of probe (e.g., capture probes) from the hybridized sample (e.g., see 134 of FIG. 1C). The G beads may be dried down on a pad in 20× SSPE and 40% trehalose (e.g., see 312 of FIG. 3A). The G-bead binding chamber may also be configured with an elution channel (e.g., see 315 of FIGS. 3A & 3B) which may also facilitate elution (e.g., at 47° C.) of the hybridized tripartite complex molecules from the beads (e.g., see 136 of FIG. 1C).

As shown in FIG. 1C, after benchtop hybridization, samples are transferred to the nCounter® instrument. Excess probes are removed through two rounds of magnetic bead-based purification. First anti-F magnetic beads bind to tripartite complexes as well as to unbound capture probes. Unbound reporter probes are washed away, and the remaining components are eluted. Second, anti-G magnetic beads bind to the reporter probes. At this state, all remaining reporter probes are hybridized to their respective target nucleic acids. Unbound capture probes are washed away. A final elution step leaves only purified tripartite complexes.

Another example uses a porous polymer matrix instead of magnetic beads. The surface can be activated by attaching oligonucleotides. These porous polymer materials are very inexpensive substrates and offer significant cost reduction compared to magnetic beads. One effective porous polymer matrixes is high density polyethylene with pore sizes of 25, 75 and 125 mm nominal.

Referring to FIG. 1A, the sample (which may now be purified of the excess probe molecules) may then be passed to an imaging surface 108 (e.g., a streptavidin surface) to be stretched and immobilized for imaging 110. For example, referring to FIG. 1D, the biotin moieties in the capture probes within the tripartite complexes may bind to the imaging surface 138. The instrument may then flow buffer and/or like fluids on the imaging surface of the microfluidic cartridge 140 (e.g., see 316 of FIG. 3A) to elongate and align the complexes on the surface. In some implementations the buffer and/or like fluid may also contain a molecule (e.g., biotinylated anti-G oligonucleotides and/or like molecules) which may facilitate binding of reporter probes in the tripartite complexes to the imaging surface 142. The instrument may then detect the complexes in the sample in order to generate a resulting graphic and/or numerical representation of the detected molecules 112. For example, the instrument may include an epifluorescence microscope configured to count the fluorescent barcodes of the reporter probes in the tripartite complexes, and to match the count to corresponding molecular targets in order to identify the molecule in the sample (e.g., see FIG. 1E).

Figure 1D:
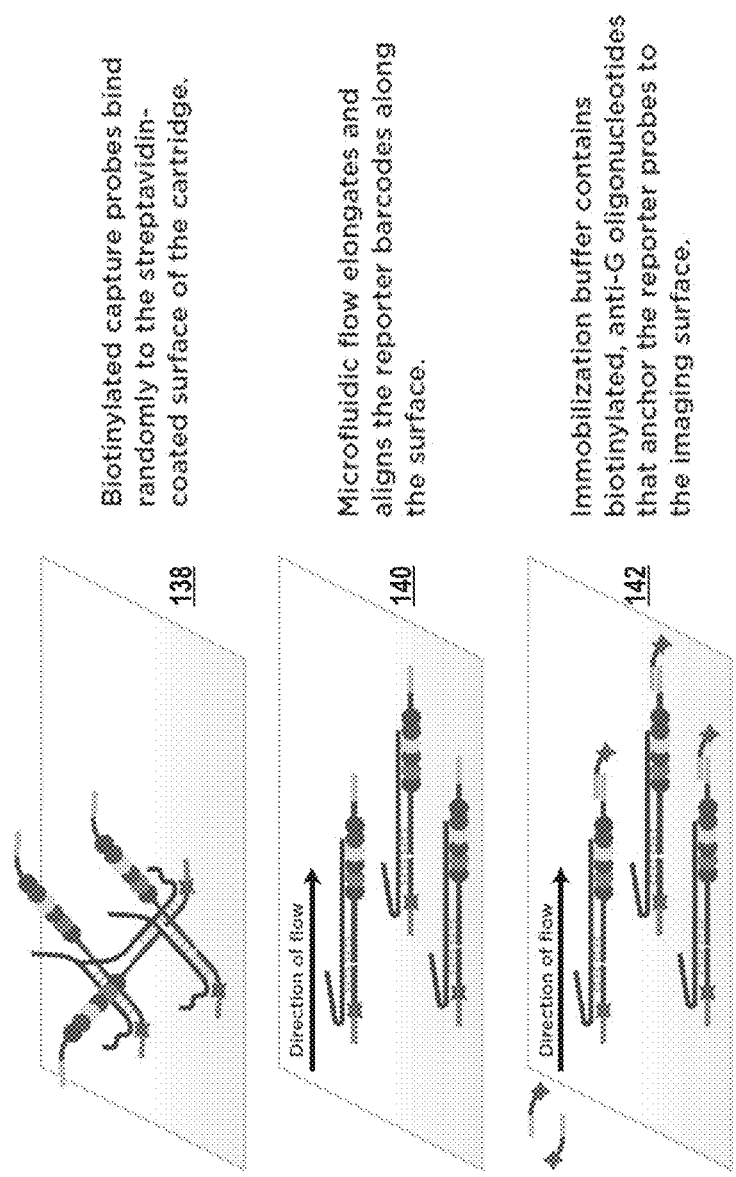

As shown in FIG. 1D, after purification, samples move to the imaging surface, which is coated with streptavidin. Biotin moieties on each capture probe bind to the imaging surface. Flow within the microfluidic cartridge then elongates and aligns the tripartite complexes. The immobilization buffer contains biotinylated anti-G oligonucleotides that anchor the reporter probes to the imaging surface.

Figure 1E:
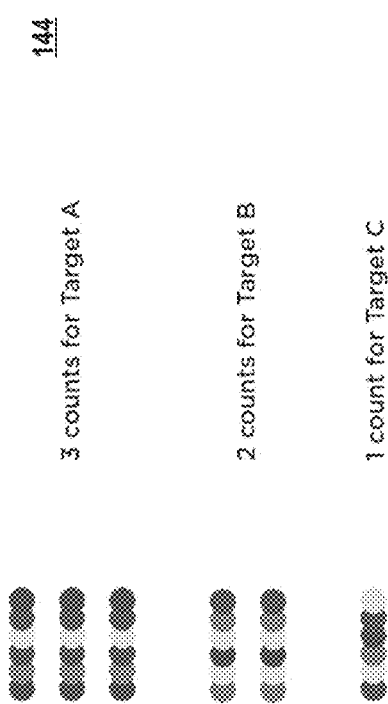

As shown in FIG. 1E, samples are imaged by an epifluorescence microscope with the nCounter® instrument. Barcodes are counted and matched with their corresponding targets. Counts for each target are exported in a comma-separated value file.

Figure 2:
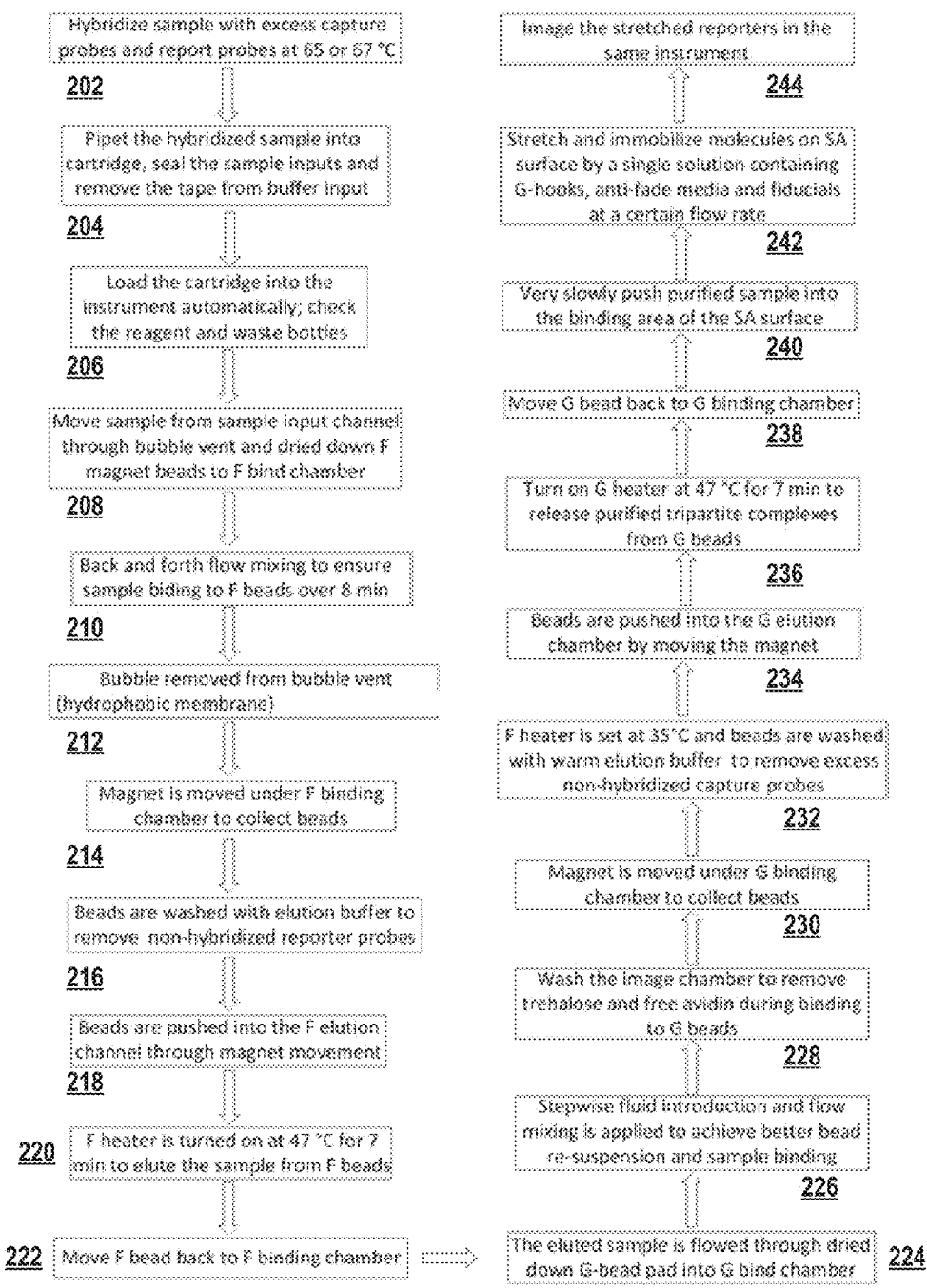
FIG. 2 shows a detailed logic flow diagram illustrating a purification and imaging process according to some embodiments.
Figure 6A:
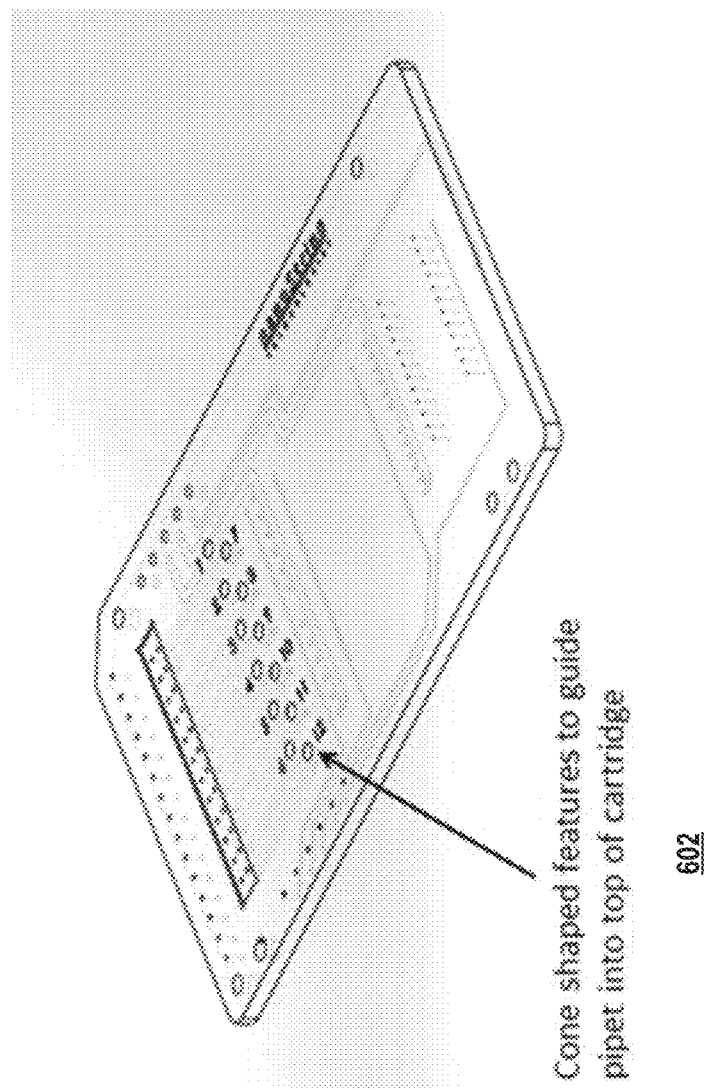
FIG. 6A shows pictorial diagrams illustrating where sample is input into the cartridge according to some embodiments.
Figure 6B:
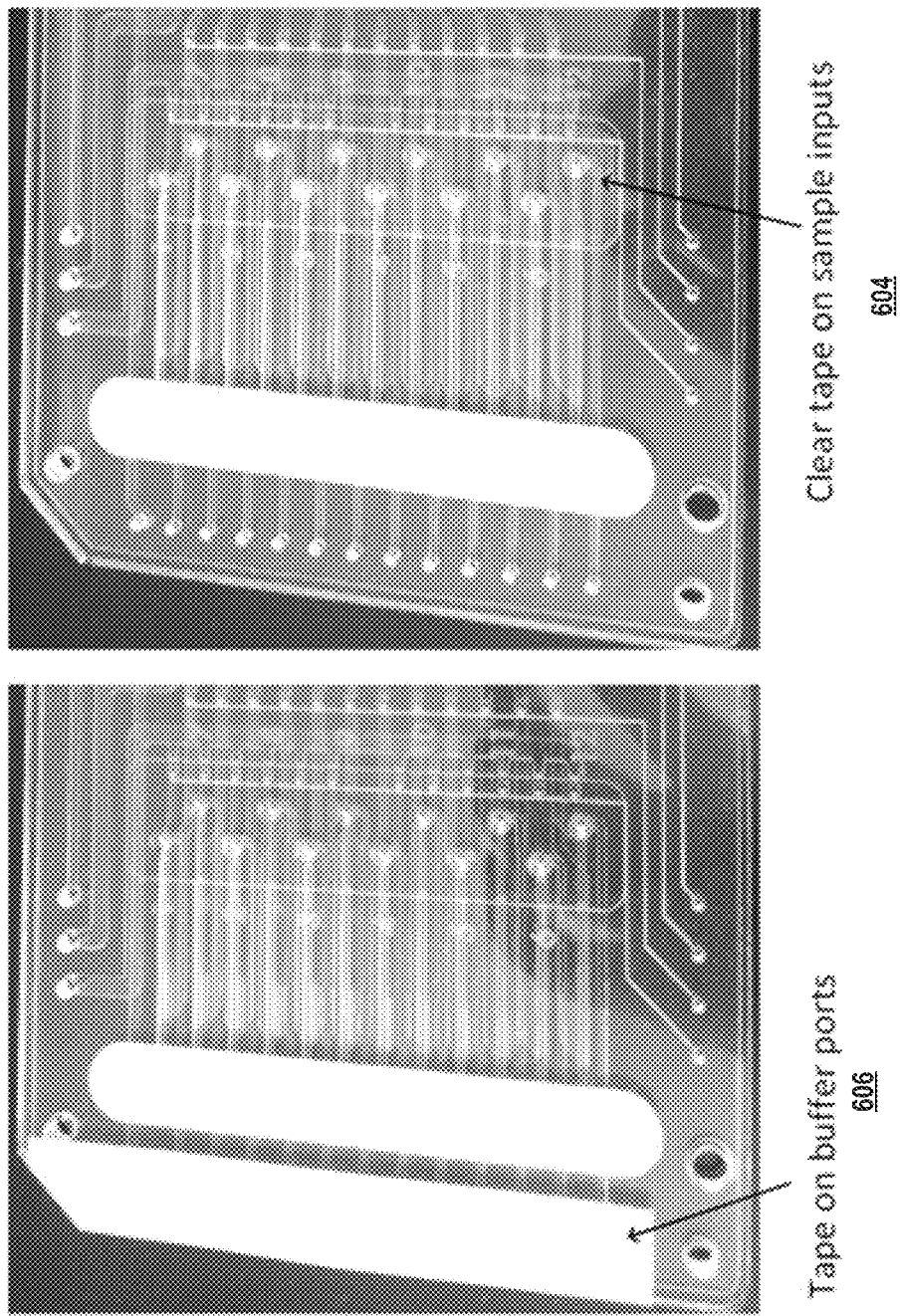
FIG. 6B shows where tape is applied after sample input and where is removed from the buffer ports according (to prevent cross contamination) to some embodiments.

FIG. 2 shows a logic flow diagram illustrating a purification and imaging process according some embodiments. For example, the user may hybridize a sample (e.g., a biological sample; see 114 in FIG. 1B) with excess capture and reporter probes 202 at approximately 65° C. The user may then place the hybridized sample (e.g., via pipetting a portion of the hybridized sample) into a sample input area 204 (e.g., also see 302 of FIG. 3A, 602 of FIG. 6A) configured to hold the biological sample. The sample input ports in the sample input area may be coned to allow for easier pipetting. The user may use a single-channel or multi-channel pipet to transfer the sample. In some embodiments, the user may seal the sample inputs (e.g., with transparent tape as shown at 604 of FIG. 6B) and may remove a seal (e.g., opaque tape as shown at 606 of FIG. 6B) from a buffer input area (e.g., see 304 of FIG. 3A) configured to receive buffer from the instrument.

Figure 7:
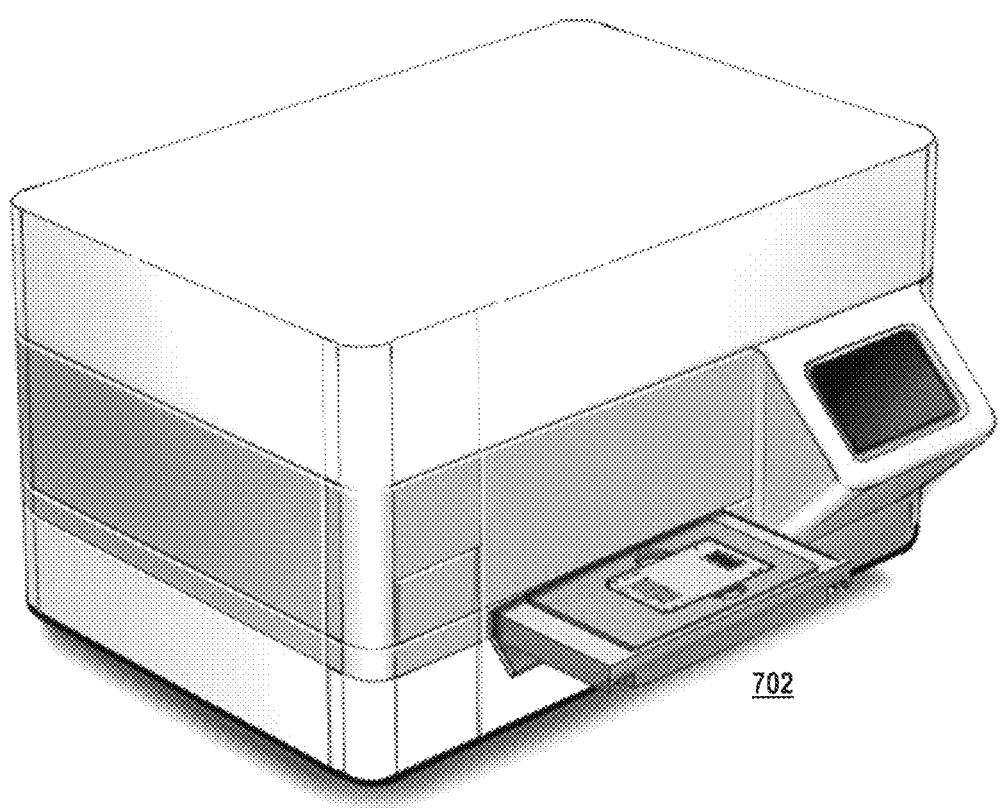
FIGS. 7-9B show pictorial diagrams illustrating an instrument according to some embodiments.
Figure 8:
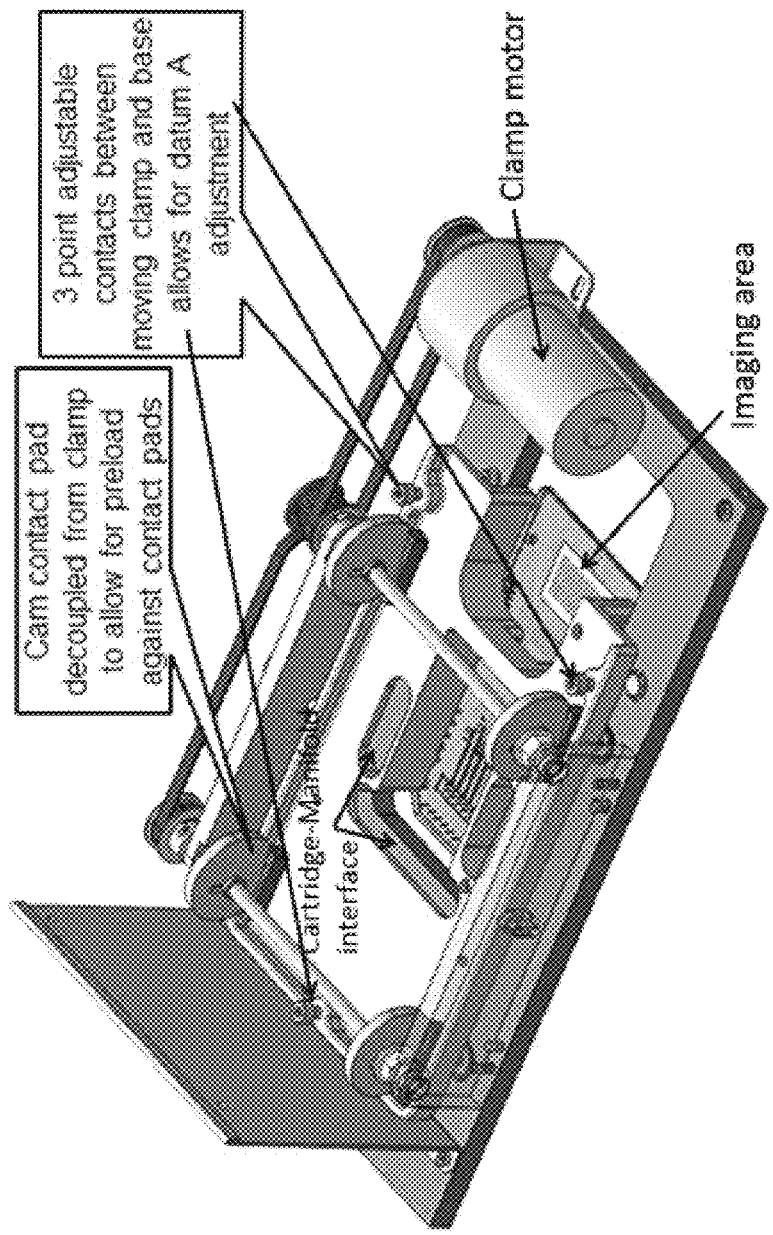

The user may load the cartridge onto a cartridge tray (e.g., tray 702 in FIG. 7) in the instrument 206. FIGS. 8-9B illustrate a clamp motor and/or other mechanisms for holding, moving, and heating the cartridge, as well as imaging the sample on the cartridge and transferring fluids to and from the cartridge. For example, the cartridge tray may be loaded into an instrument nest as the tray moves inside the device, and may connect to a fluidic manifold and imaging reference surfaces operatively connected above the cartridge, with heaters and bottom contact points positioned below the cartridge and configured to push the cartridge up against the fluidic manifold, and imaging reference points with cam mechanism and springs (e.g., see FIG. 8 and FIG. 9B). Additionally, the instrument may include a fluidic manifold 906 operatively coupled to off-card buffer input valves 902 and waste valves 904, which may connect to the cartridge and provide fluids to the cartridge, or remove used fluids from the cartridge, respectively.

Figure 5:
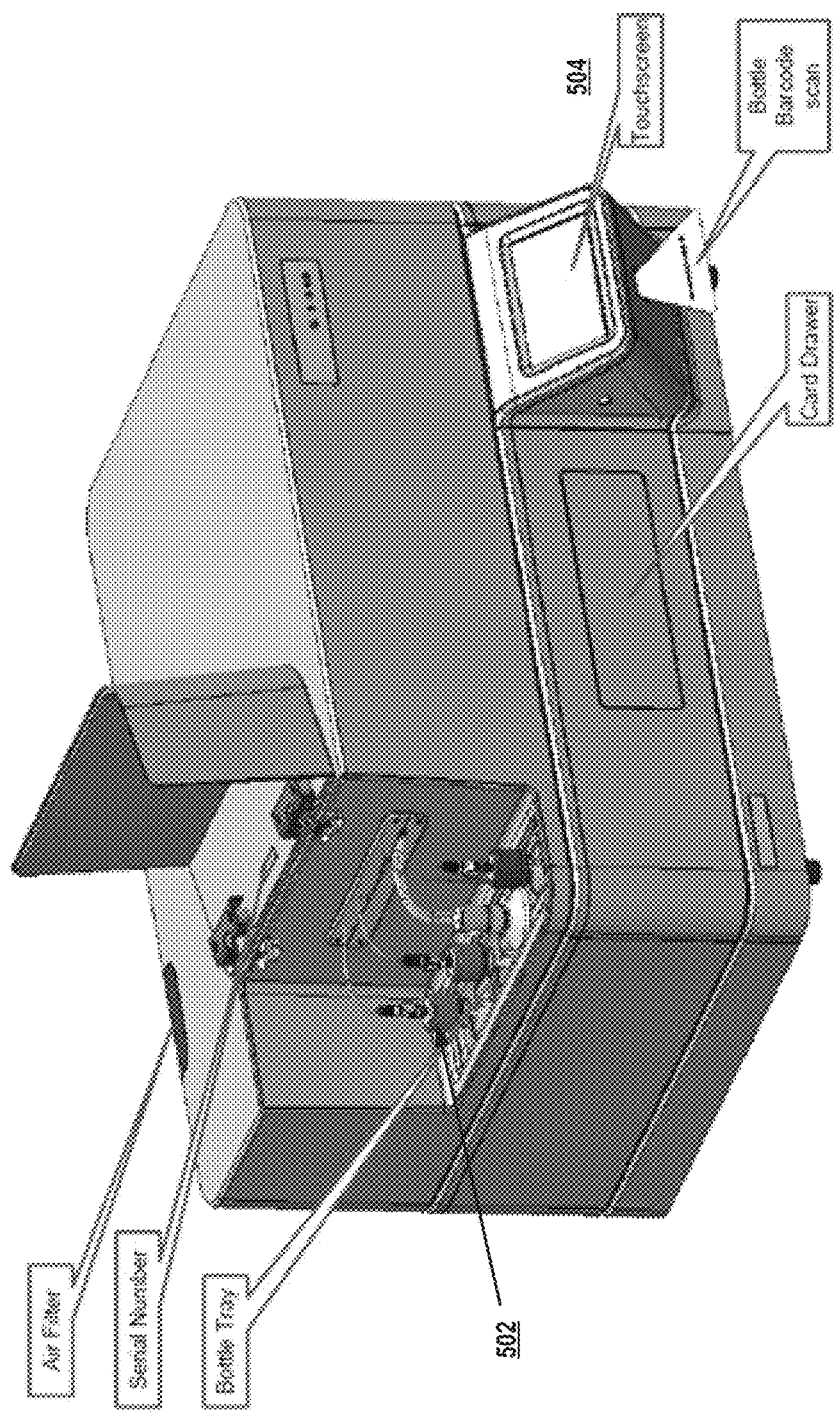
FIG. 5 shows a pictorial diagram illustrating a machine that carries out both fluidics and imaging functions.

The device may automatically determine whether the cartridge has been correctly loaded, and may also make sure that reagent (e.g., buffer) and waste bottles (e.g., 502 in FIG. 5) are correctly connected to the cartridge, and that the reagent bottles have sufficient levels of buffer and/or similar fluids. In some embodiments, the user may be prompted to replace reagent bottles if more fluid is required (e.g., via screen 504 in FIG. 5), and/or the like.

Figure 10:
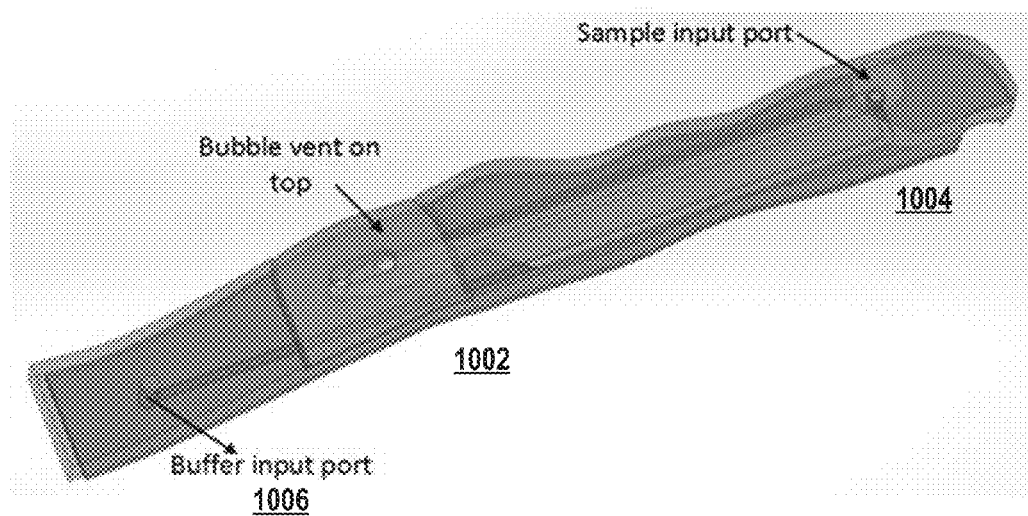
FIG. 10 shows a pictorial diagram illustrating an imaging cartridge according to some embodiments.
Figure 11:
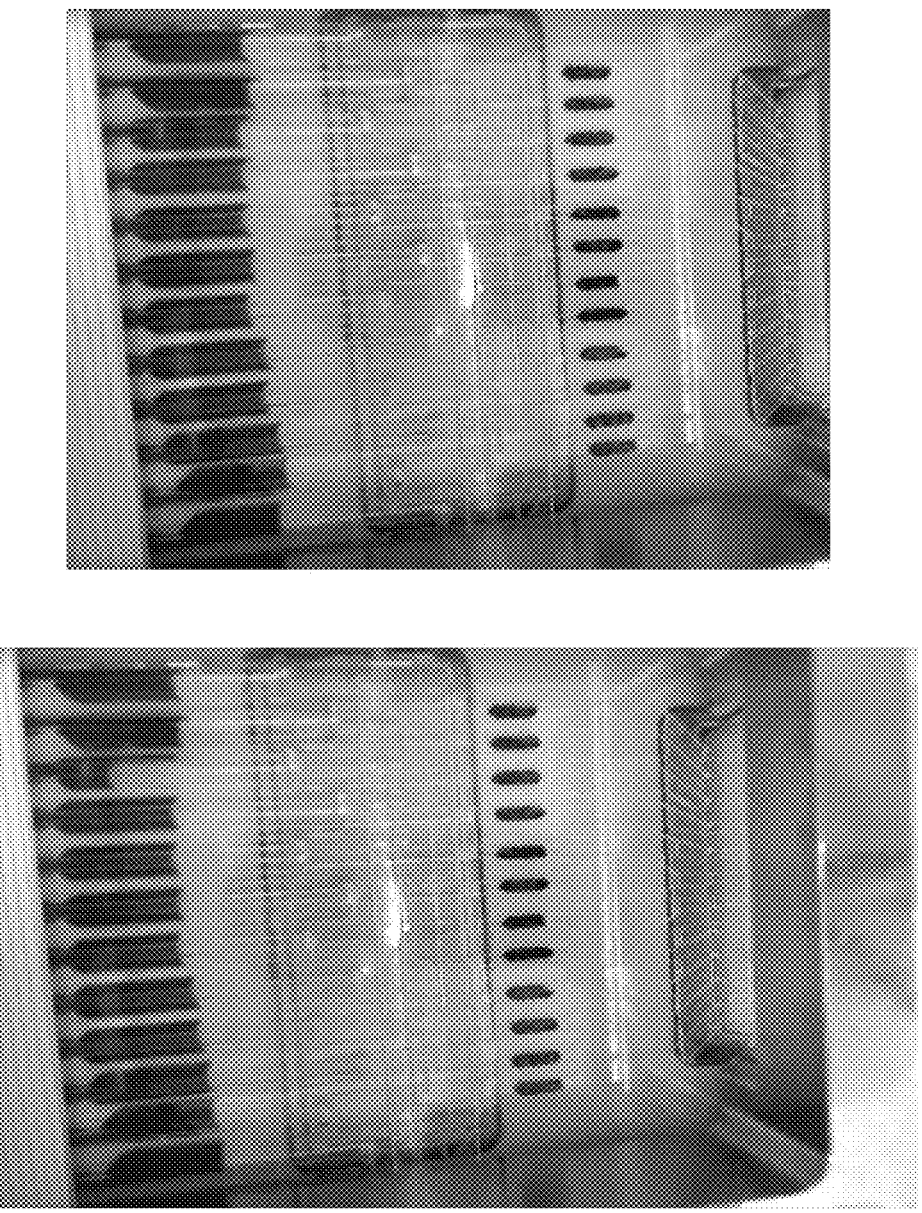
FIGS. 11-12 show pictorial diagrams illustrating purifying a sample according to some embodiments.

The instrument may then move the sample from the sample input area via a flow (e.g., 304), through a bubble vent and/or trap (e.g., a hydrophobic membrane; see 306 in FIG. 3A) configured with an air bubble to separate the sample from the buffer. This bubble prevents sample dispersion by separating the two liquids. In some implementations binding chambers (e.g., such as the F binding chamber and the G binding chamber) can hold magnetic beads and/or other molecule-binding apparatus for purification of a sample. The F binding chamber may hold dry F magnetic beads which may be configured to bind to excess probe molecules (e.g., excess reporter probe molecules) in the hybridized sample (e.g., see 126 of FIG. 1C). The instrument may move the sample & beads (e.g., 15 µL back and forth repeatedly) with a pump over the porous bead pads 210 in order to better facilitate resuspension and binding of the F beads to the excess capture probes and to the sample molecules (e.g., see FIG. 11). The F beads may settle out of the solution; therefore the movement may be necessary in order to keep them suspended in the solution. The bubble vent (e.g., see 1002 in FIG. 10) may be physically positioned between the sample input area (e.g., see 1004 in FIG. 10) and F-binding chamber (e.g., see 308 in FIGS. 3A & 3B), and may be configured to eliminate bubbles, especially the large bubble between the sample and buffer after mixing and binding has finished. However, it is important the bubble between the sample and buffer does not pass the bubble vent during this mixing process in order to maintain sufficient backpressure to pull the sample back instead of pulling air through the bubble vent.

In some embodiments, moving a magnet pair back and forth across the chamber may be done instead of moving the sample back and forth with flow. Magnets may be used in pairs to generate a complex magnetic field suitable for mixing. The dead spot above and between the magnets may be critical for good mixing. The magnet speed may be related to chamber size and bead amounts (for example).

Figure 12:
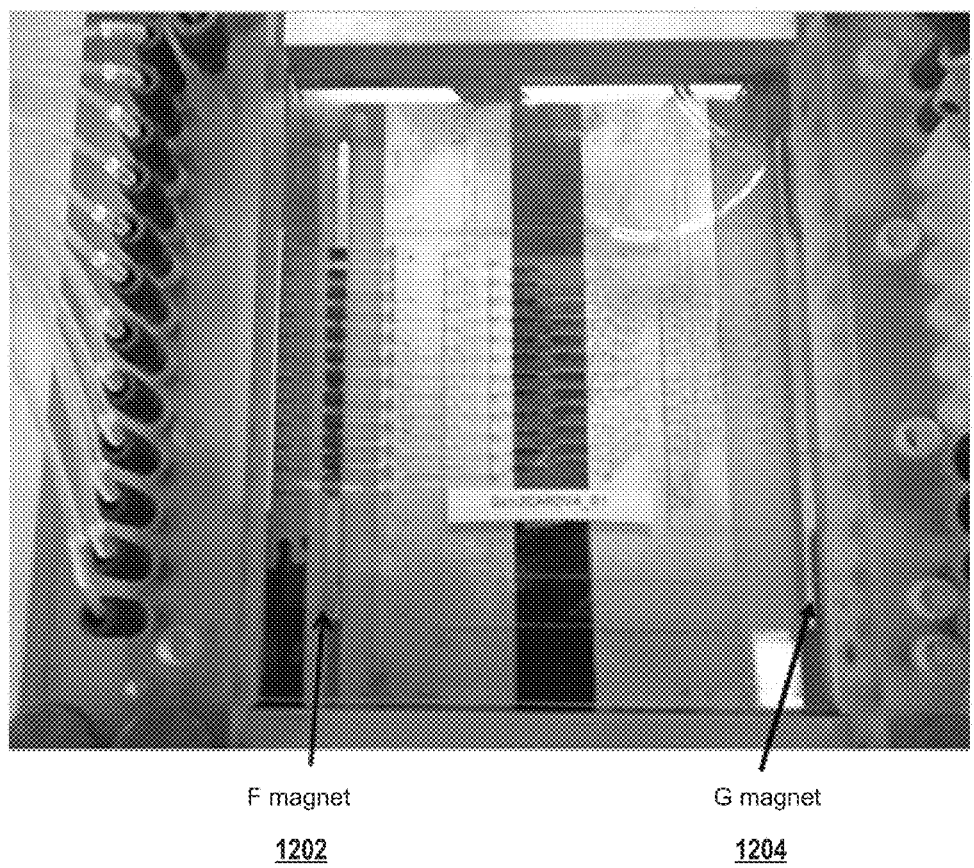
Figure 13A:
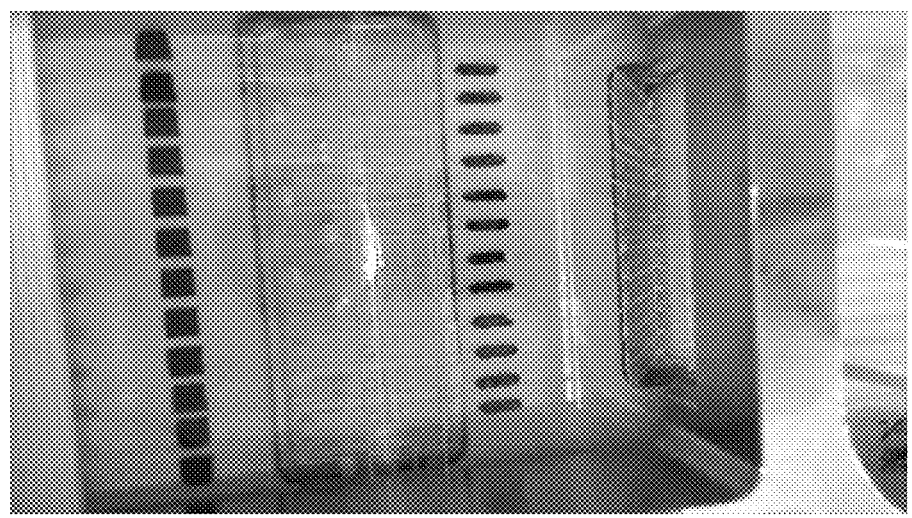
FIGS. 13A-14 show pictorial diagrams illustrating purifying a sample according to some embodiments.

The binding process may, in some embodiments, last at least 8 minutes (for example). The bubble from the bubble vent may then be removed 212 during the mixing of the hybridized sample to the F beads. A magnet (e.g., an F magnet; see 1202 in FIG. 12) in the instrument configured to move parallel to the cartridge, may be moved under the F binding chamber in order to collect the F beads 214, and to hold them in place as they are washed with an elution buffer 216 added from the buffer input area. The elution buffer may facilitate removal of at least one type of non-hybridized probes (e.g., non-hybridized reporter or capture probes; (e.g., see 128 of FIG. 1C)) from the F beads. During the multistage wash step, beads may be moved around in the F binding chamber by moving the magnet (e.g., see 1302 in FIG. 13A). This movement and spreading out of the beads may allow for better washing of the captured beads.

Figure 13B:
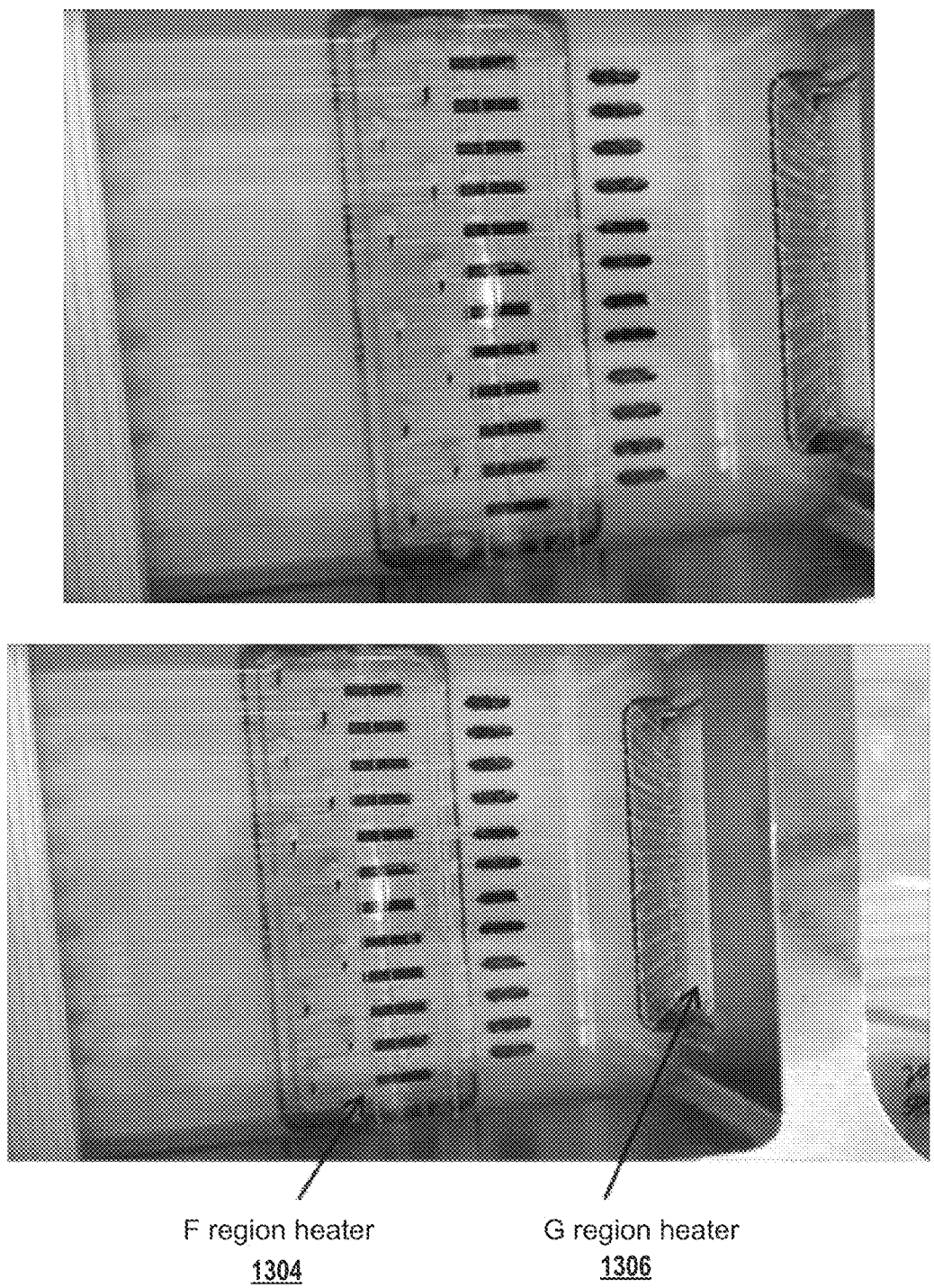
Figure 14:
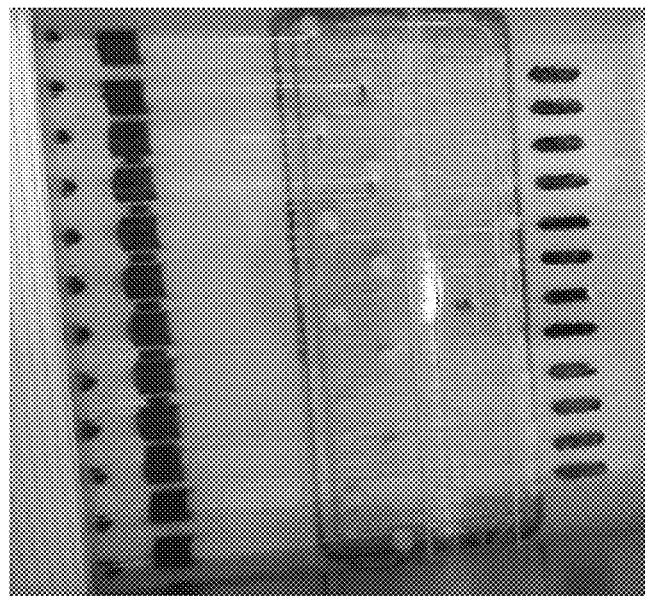
Figure 14:
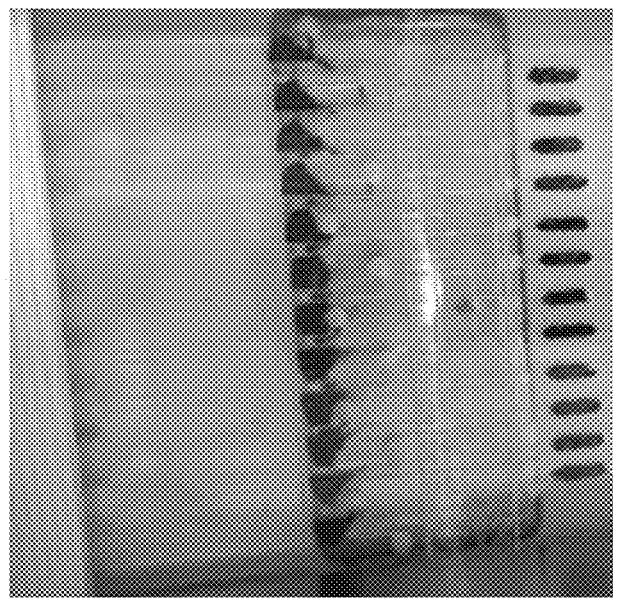

The beads, via the magnet, may then be pushed into an F elution channel 218 (e.g., also see 310 of FIGS. 3A and 3B), which may be connected to a heater (e.g., an F heater; see 1304 in FIG. 13B) which may be configured to heat the F beads 220 (e.g., to 47° C. for four minutes) in order to elute the sample molecules from the F beads (e.g., see 130 of FIG. 1C). The F beads, after the heating process, may be returned to the F binding chamber 222 (e.g., see FIG. 14) as the eluted sample is moved into a second binding chamber 224 (e.g., a G binding chamber; see 314 in FIGS. 3A or 3B), configured to facilitate the binding of a second set of dry magnetic beads (e.g., G magnetic beads) to the hybridized tripartite complex molecules.

Figure 15:
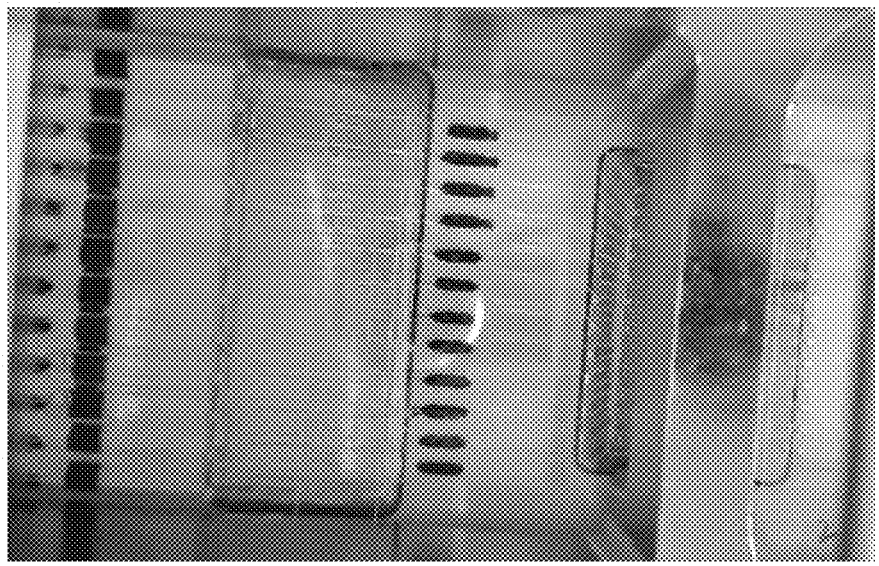
FIGS. 15-17 show pictorial diagrams illustrating purifying a sample according to some embodiments.
Figure 15:

A stepwise fluid introduction and flow mixing process may be utilized with the G magnetic beads and the eluted sample in order to achieve proper bead re-suspension and sample binding 226. The G magnetic beads may bind to reporter probes and/or other probes which may still be attached to the sample molecules (e.g., see 132 of FIG. 1C). For example, introduction of the F-eluted sample into the G binding chamber may be performed in repeated small steps of 2 µL forward followed by 1 µL backward. The back and forth of fluid may help re-suspend the G beads and make the systems insensitive to small differences in bead pad/bead pocket size. This back and forth mixing can occur through the porous pad. In some embodiments, an exact flow profile may be +5 µL, −4 µL, +5 µL, −4 µL, +5 µL. Binding may occur for a specified period of time, before another 7 µL is introduced. In some embodiments (e.g., see FIG. 15), elutions may be flowed one lane at a time 1502 until all elutions have been flowed into lanes 1504 (e.g., the process may take 7 minutes).

Figure 16:
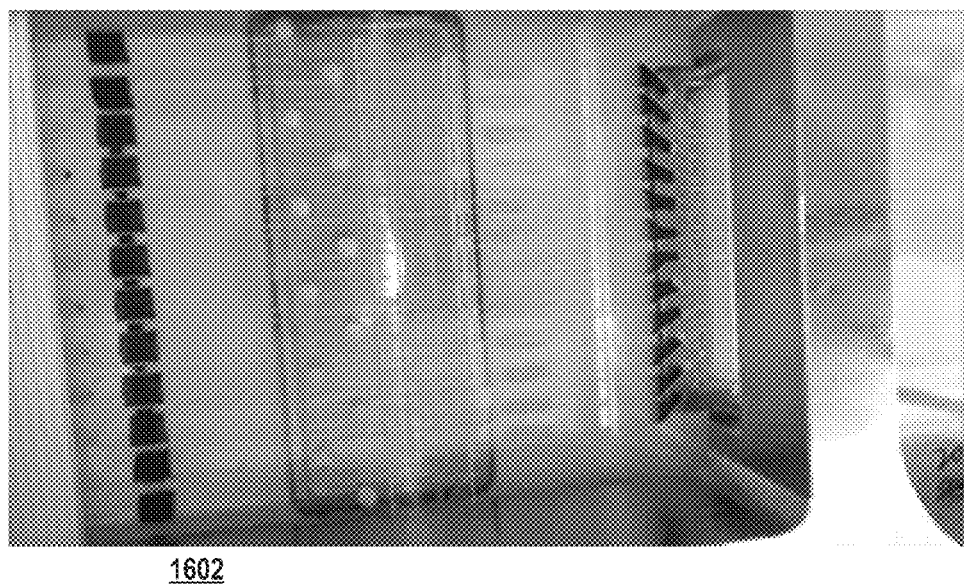
Figure 16:
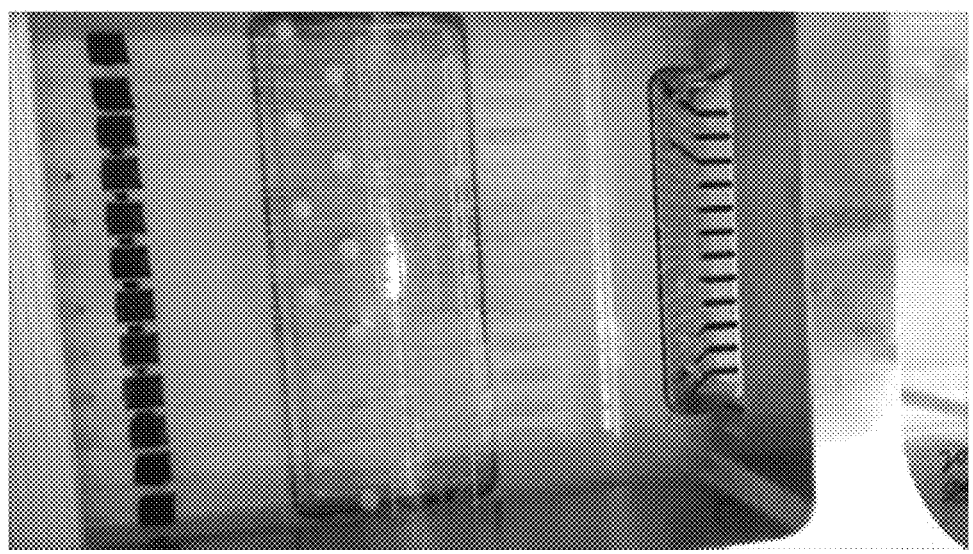
Figure 17:
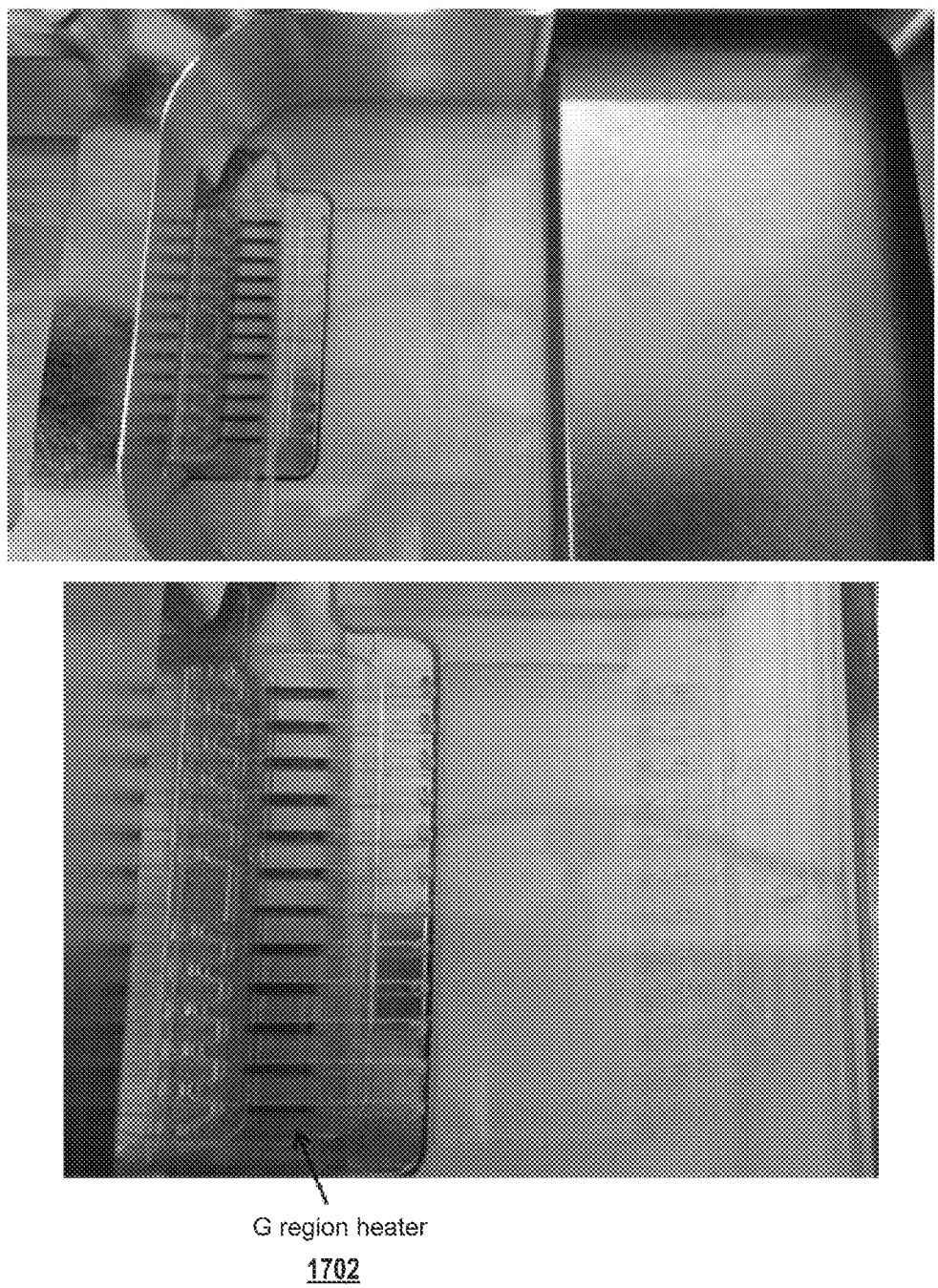

An imaging chamber, meanwhile, may be washed 228 in order to remove molecules (e.g., trehalose and free avidin) while the G beads are bound to the eluted sample. A magnet (e.g., a G magnet; see 1204 in FIG. 12) may be moved under the G binding chamber 230 in order to collect all of the G beads and hold them as a heater (e.g., the F heater) heats the F binding & elution chamber 232 (e.g., to 35° C.). Meanwhile an elution buffer (e.g., warmed by the heater) may be washed over the G beads in order to facilitate removal of excess non-hybridized capture probes from the G beads (e.g., see 134 of FIG. 1C). The beads may then be moved to a G elution chamber (e.g., see 315 in FIGS. 3A and 3B and 1602 and 1604 in FIG. 16) via the magnet 234, such that a second heater (e.g., a G heater; see 1306 in FIG. 13B and 1702 in FIG. 17) configured to release the purified sample (e.g. tripartite complexes) from the G beads, may be initiated 236.

Figure 18:
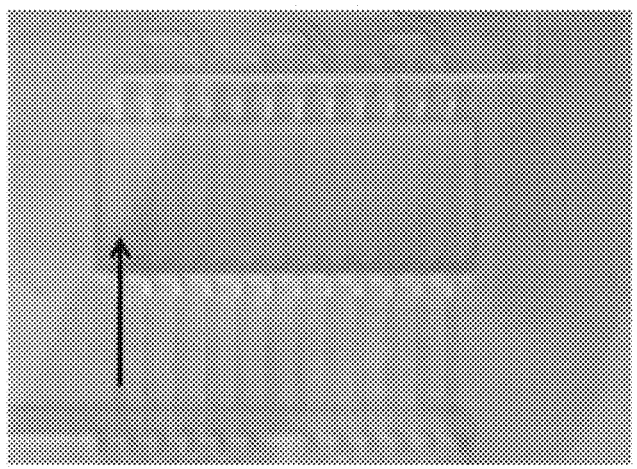
FIG. 18 show pictorial diagrams illustrating moving a purified sample to an imaging surface according to some embodiments.

The G heater may be run at 47° C. for 4 minutes to release the sample from the beads (e.g., see 136 of FIG. 1C). The magnet may then move the G beads back to the binding chamber 238, and the purified sample may be moved 240 (e.g., see FIG. 18) into a binding area of an SA surface (e.g., see 316 in FIGS. 3A and 3B). Flow rate into the chamber may be performed in steps that are about half the volume of the chamber or less (e.g., approximately 0.25 µL, every 78 seconds). The small elution volume and the controlled flow (using a syringe pump instead of gravity), allows for faster and more efficient binding.

Figure 19A:
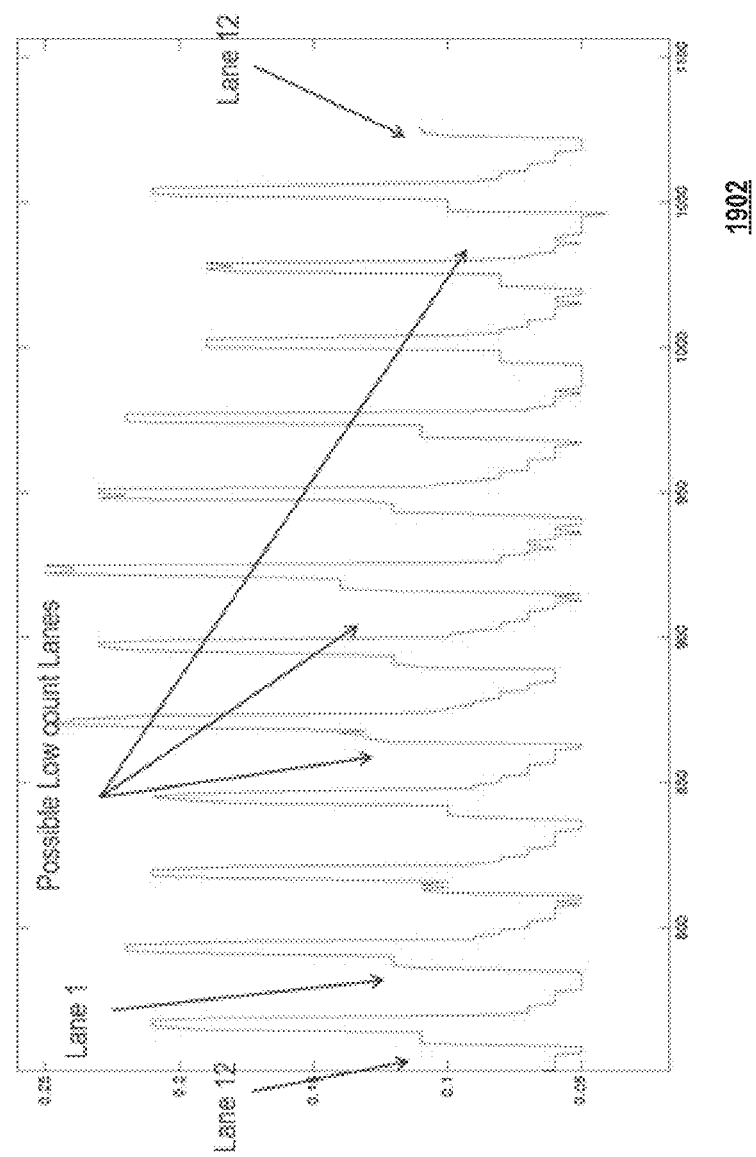
FIGS. 19A-B show graphs illustrating adding the sample to the imaging surface according to some embodiments.
Figure 19B:
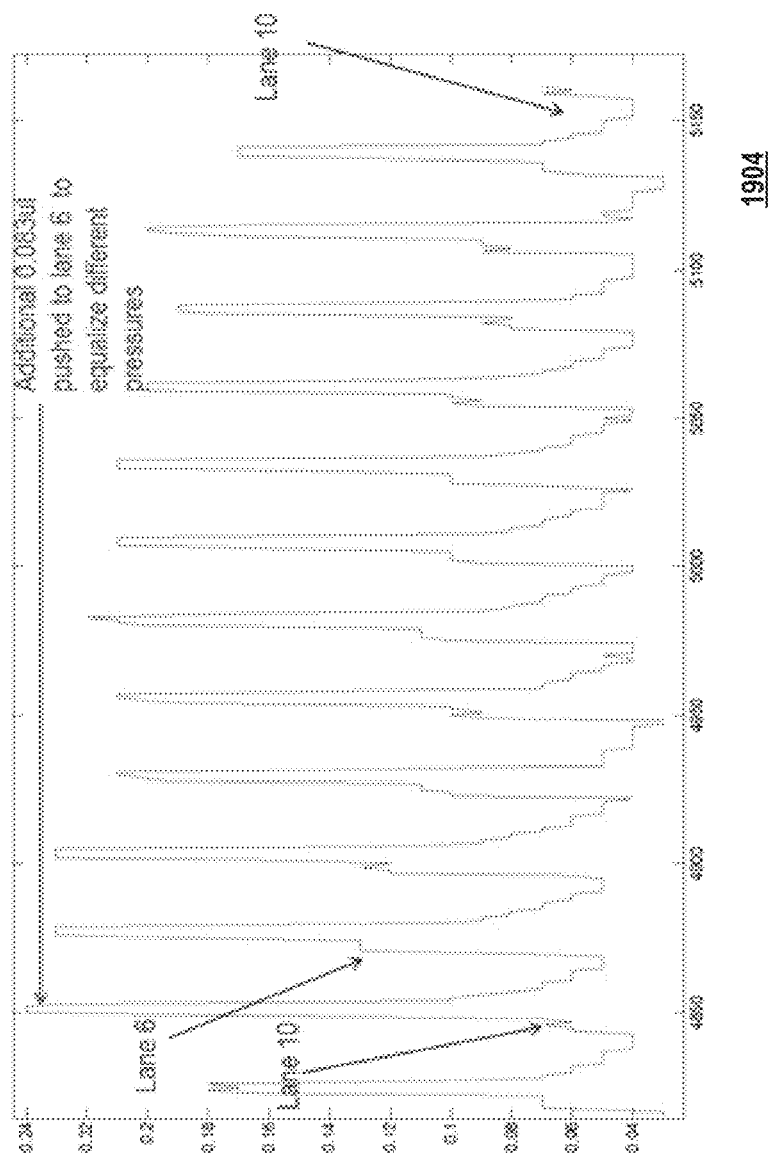

In some embodiments, dynamic sequencing of twelve lanes may be performed in order to equalize flow volume of eluted samples binding to SA surface. For example, approximately 0.25 µL, may be flowed every 76 seconds on each lane. The stepping may be done in sequence: 0.25 µL, steps every 6.3 seconds per lane in a sequence (e.g., lanes one through twelve), which may result in 12*6.3=75.6 seconds of wait time on every lane for every 0.25 µL, step. Because twelve valves may be opened and closed in sequence for twelve separate lanes and move only a small volume, the displacement volume of each individual valve may affect the lane to lane reporter count variability. The variation in displacement volume from the pump by itself may not affect variability; however the difference in displacement volumes due to the valves may have a big effect on variability. The displacement of each valve may be estimated (e.g., see 1902 in FIG. 19A) by using the pressure reading difference of closed vs open state of the valve. Minimization of lane to lane variability may require minimization of displacement volume variability by re-ordering the lanes. To minimize the variability, the instrument may start pushing from the valve that has highest displacement volume then the second highest and so forth finishing with the smallest. The transition from smallest to highest may have the most negative effect; to correct that, the instrument may be configured to push an extra 0.083 µL on that single lane (e.g., 0.333 µL instead of 0.25 µL; see 1904 of FIG. 19B).

Figure 20:
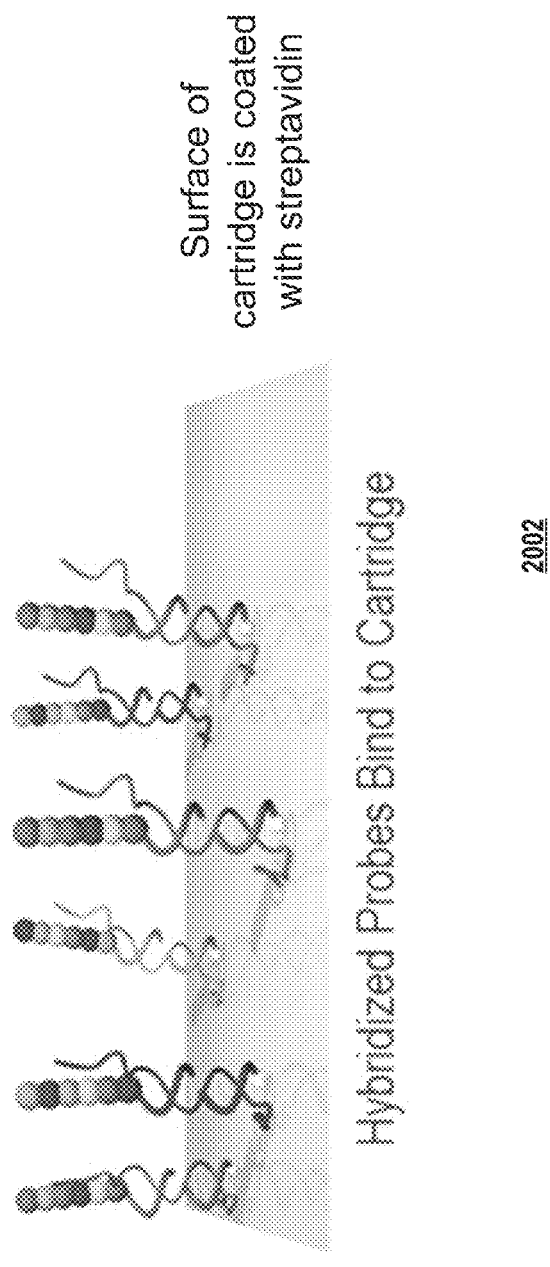
FIGS. 20-21 show pictorial diagrams illustrating binding a purified sample to an imaging surface according to some embodiments.
Figure 21:
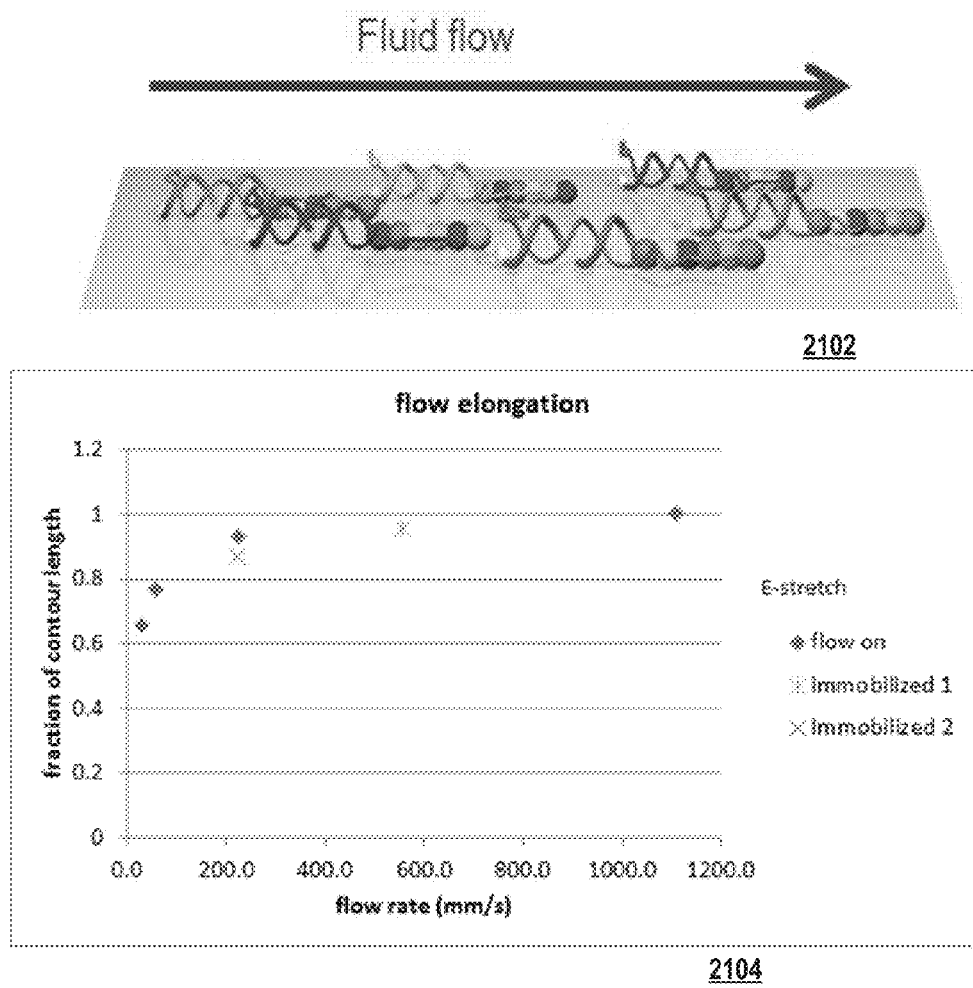

In some embodiments (e.g., in FIG. 20), the SA surface may be a surface coated with streptavidin, and may bind to the hybridized probes in the sample 2002 (e.g., see also 138 in FIG. 1D). There, the molecules in the purified, second-eluted sample may be stretched and immobilized 242 on the SA surface (e.g., also see 2102 in FIGS. 21 and 140 & 142 of FIG. 1D), e.g., via a single solution comprising at least G-hooks (biotinylated anti-G 15mer oligo), mounting media (anti-fade), and fiducials (multispectral biotinylated fluorescent 100 nm beads, i.e., diffraction limited), and being added to the SA surface at a particular flow rate (e.g., see 2104 in FIG. 21, which is a graph indicating flow rates that may be utilized). The G hooks are used to immobilize down the second end of the reporter during stretching. The mounting media is present to prevent photo bleaching and photo-destruction of the DNA (due to light interaction with dyes that create free-radicals that can break the DNA backbone). The fiducials produce a fluorescent signal (in all channels) that is used to align images. G-hooks, mounting media, fiducials, and the stretching buffer were required to be in separate solutions in previously-described electrostretching-based immobilization processes. In some embodiments, the process may replace four buffers and may eliminate the need for electrodes and a power supply. It may also eliminate a G-hook contamination problem, which is caused by G-hooks slicking to the electrodes in previous designs and carrying over into subsequent sample runs. The instrument may then detect the stretched molecules 244 from the SA surface on the cartridge and produce an output (e.g. an image, a report, and/or the like) for the user (e.g., see 144 of FIG. 1E). In some embodiments, the instrument may have a low cost optics subcomponent that uses a three LED illumination system.

The instrument may also perform binding gradient and area optimization based on density. The binding to the Streptavidin surface may generate a reporter binding gradient over the channel—higher density at one end (inlet) with gradual decrease toward the other end (outlet). Based on the reporter density determined by an initial scanning survey, the location of imaging area may be selected for the optimal data collection. Selecting the final scan area in the high density side (close to the inlet end) may generally collect more data. However, in the case of too high binding density, the scan may start from a less dense area by moving the scan area farther from the inlet end. This scheme increases the dynamic range of sample concentration.

During imaging, mounting media may be exchanged to minimize photo-destruction and minimize non-specific binding of residual non-functional reporters by eliminating free reporters. If any free reporters are left floating free in the imaging chamber, the flow of imaging buffer wash them out, thus preventing binding via G-hooks in solution.

Additional teaching relevant to the present invention are described in one or more of the following: U.S. 2011/0086774, U.S. 2011/0145176, U.S. 2011/0201515, U.S. 2011/0229888, U.S. 2013/0004482, U.S. 2013/0017971, U.S. 2013/0178372, U.S. 2013/0230851, U.S. 2013/0337444, U.S. 2013/0345161, U.S. 2014/0005067, U.S. 2014/0017688, U.S. 2014/0037620, U.S. 2014/0087959, U.S. 2014/0154681, U.S. 2014/0162251, U.S. 2014/0371088, U.S. 2015/0072021, U.S. 2015/0252440, U.S. Pat. Nos. 7,473,767, 7,919,237, 7,941,279, 8,148,512, 8,415,102, 8,492,094, 8,519,115, 8,986,926, 9,066,963, and U.S. Pat. No. 9,181,588, each of which is incorporated herein by reference in its entirety.

The following example is offered by way of illustration and not by way of limitation.

EXAMPLE

Embodiments of the present disclosure provide superior detection and quantification of gene expression and protein synthesis.

Figure 22:
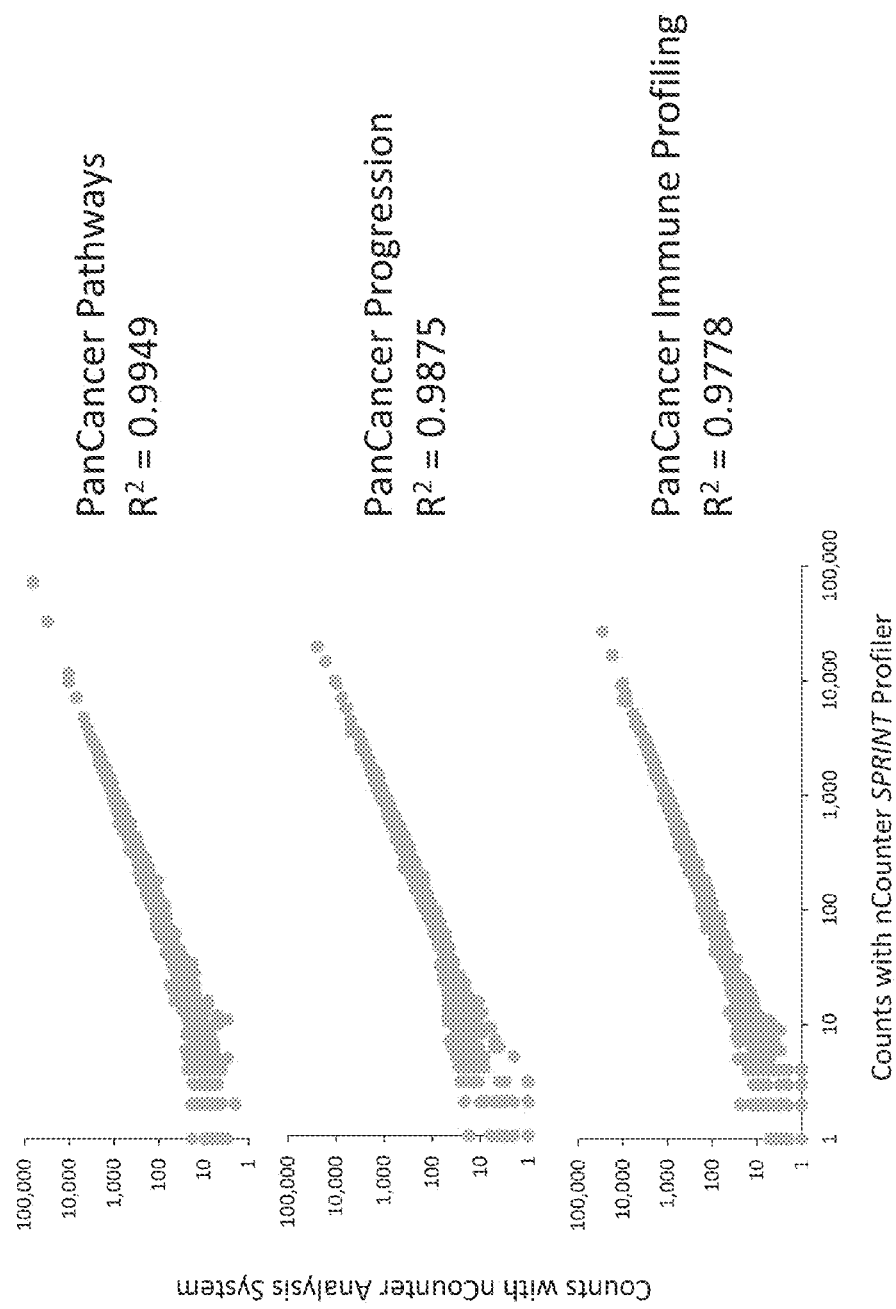
FIG. 22 shows graphs comparing results obtained with the nCounter Analysis System and results obtained according to some embodiments of the present invention for three nCounter® PanCancer Panels.
Figure 23:
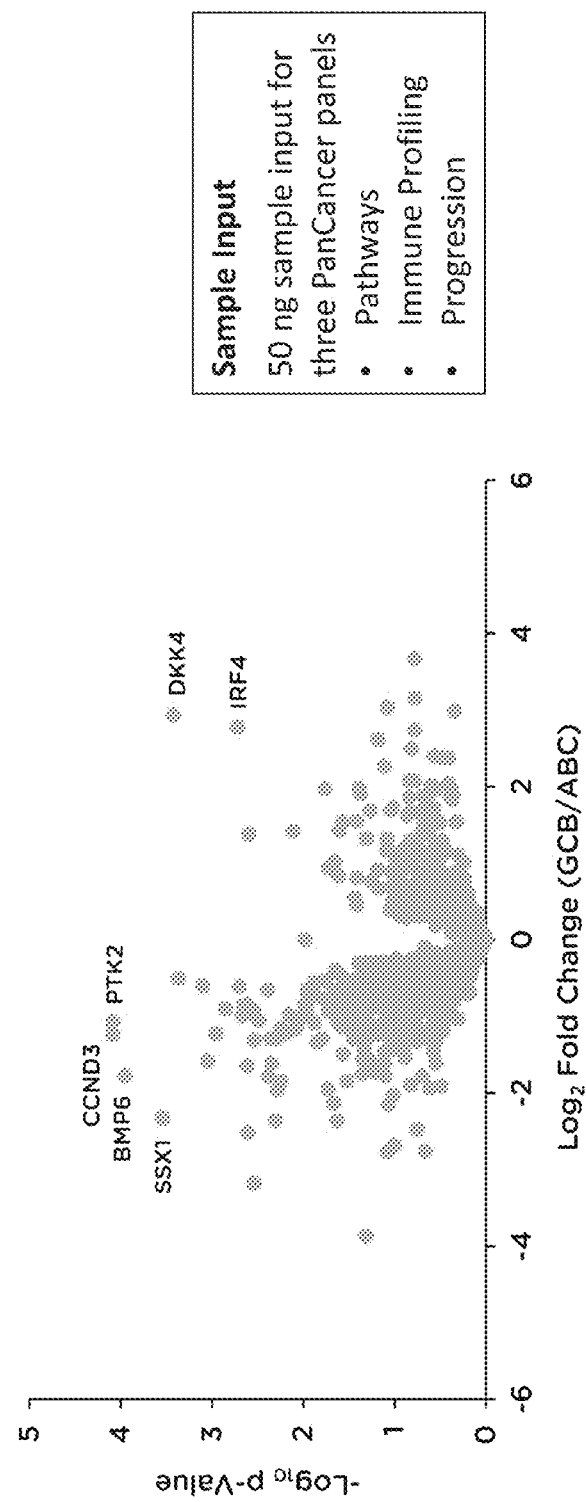
FIG. 23 shows a graph illustrating differential gene expression data obtained according to some embodiments of the present invention.
Figure 24:
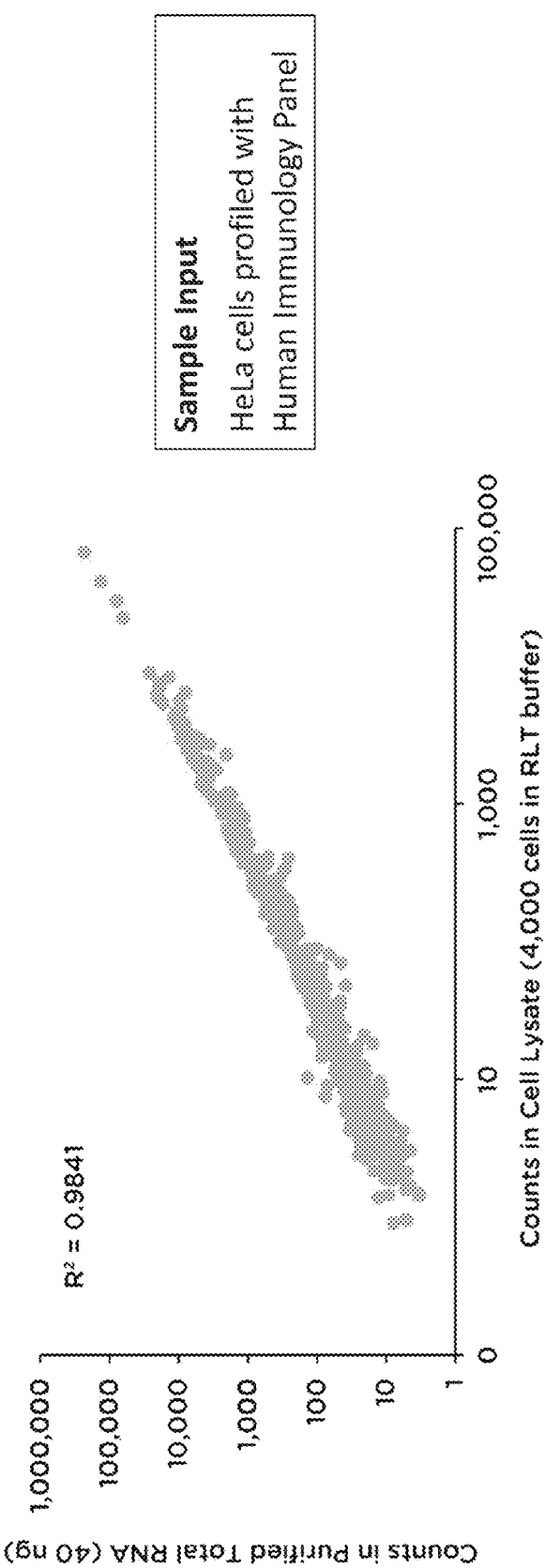
FIG. 24 shows a graph illustrating detection of total RNA or raw cell lysates.
Figure 25:
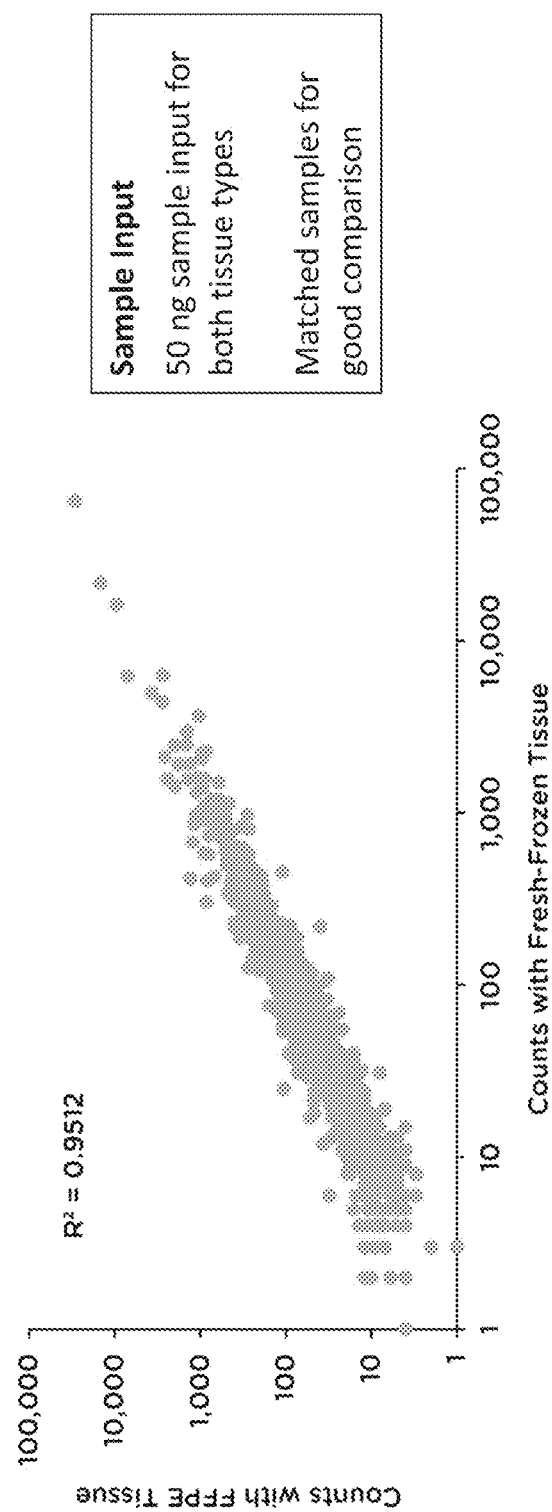
FIG. 25 shows a graph illustrating detection of total gene expression from fresh-frozen tissue or from Formalin-Fixed Paraffin-Embedded (FFPE) tissues.
Figure 26:
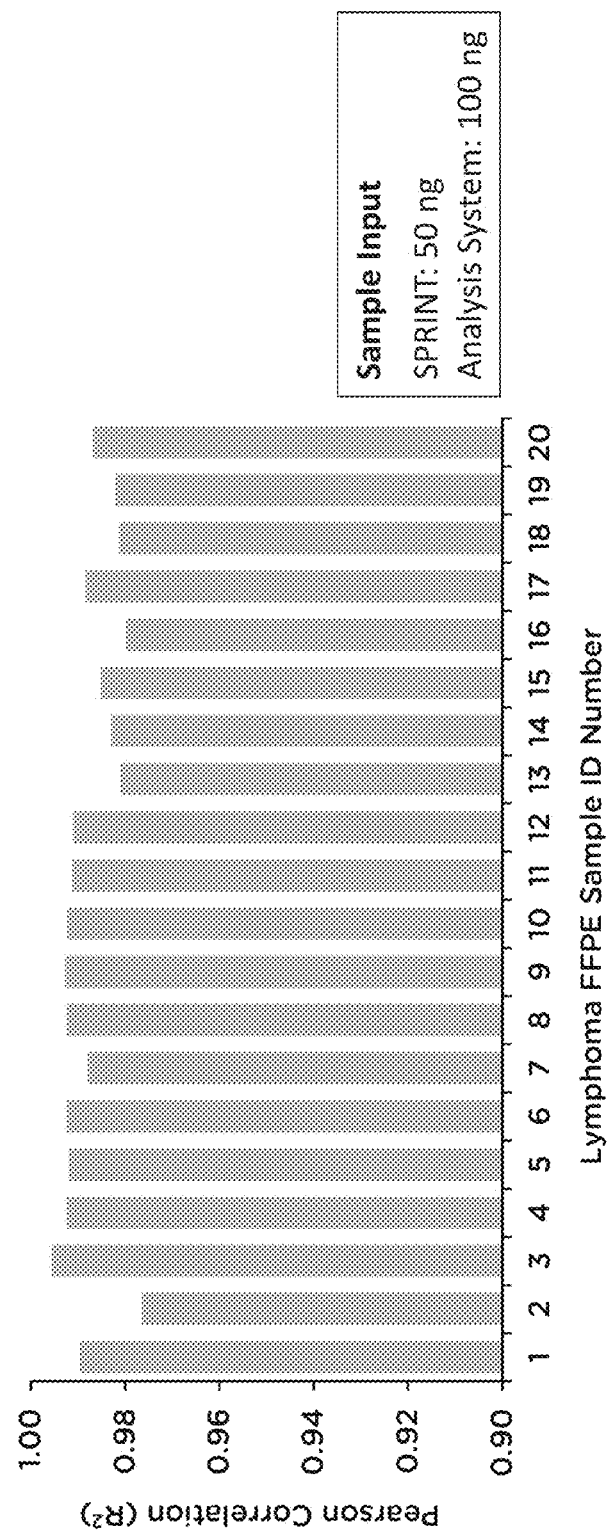
FIG. 26 shows a graph comparing results obtained with the nCounter® Analysis System and results obtained according to some embodiments of the present invention for the PanCancer Progression Panel.
Figure 27:
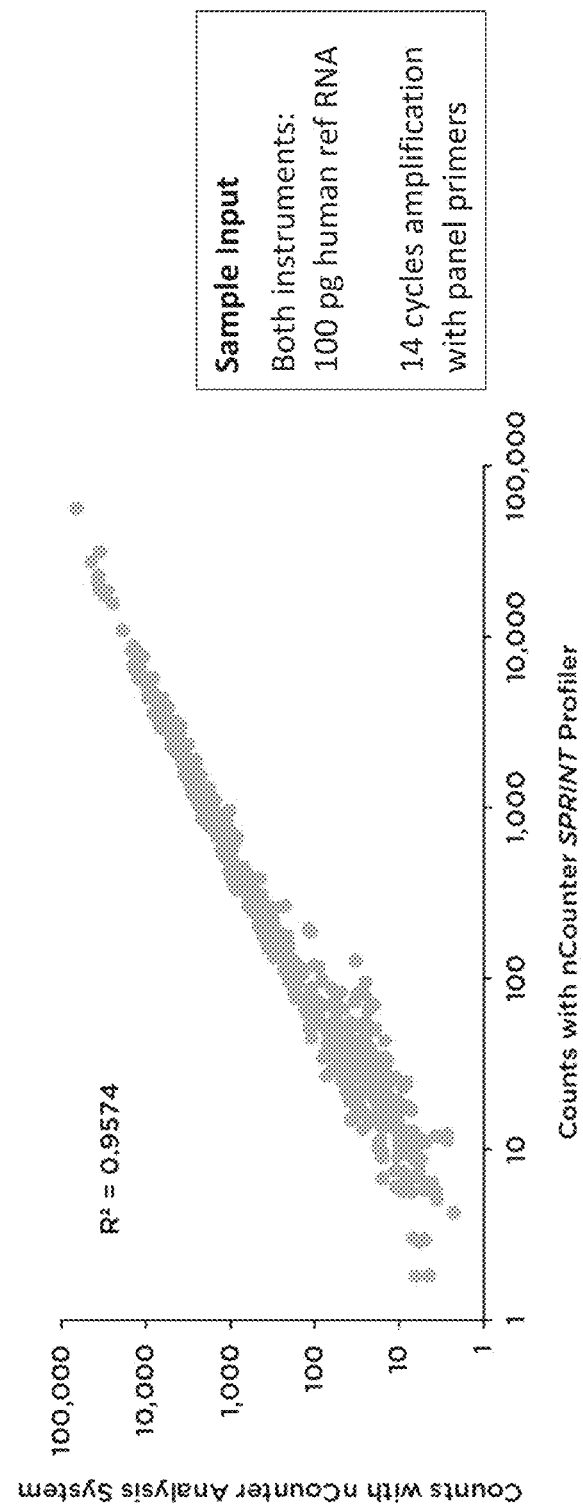
FIG. 27 shows a graph comparing results obtained with the nCounter® Analysis System and results obtained according to some embodiments of the present invention for the Human Immunology Panel
Figure 28:
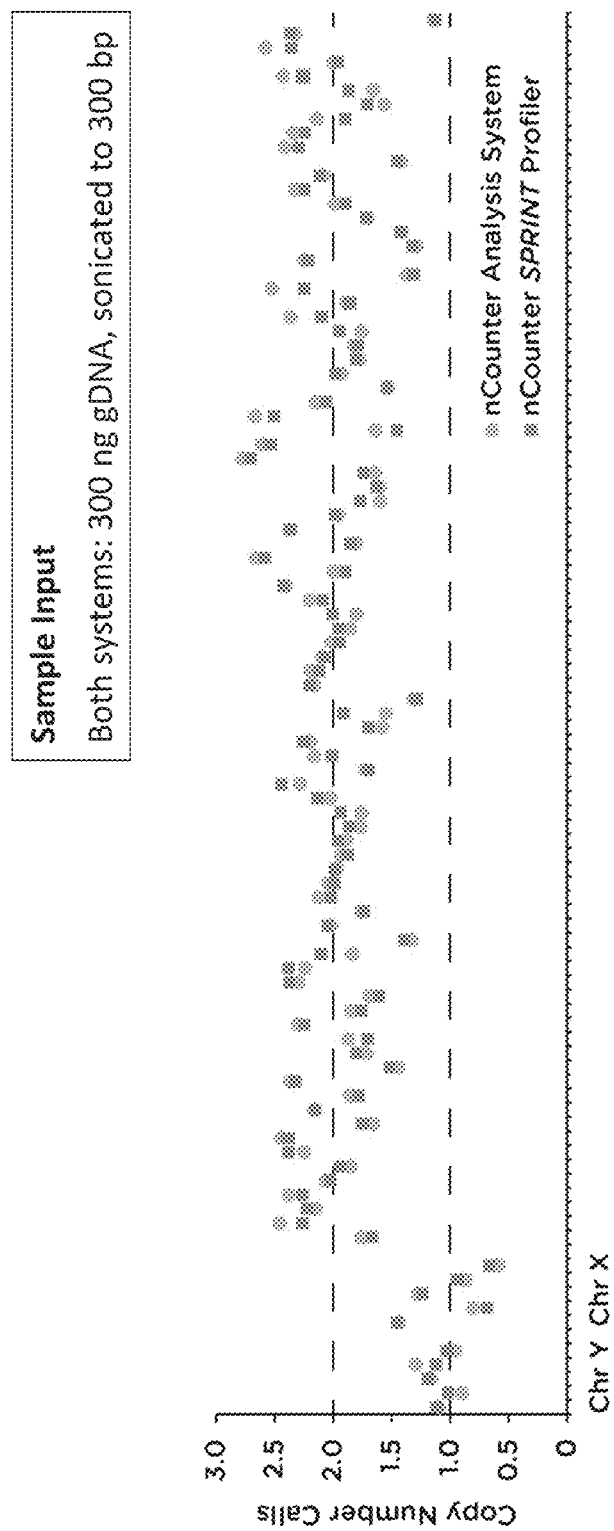
FIG. 28 shows a graph comparing results obtained with the nCounter® Analysis System and results obtained according to some embodiments of the present invention in a copy number variation (CNV) assay.
Figure 29:
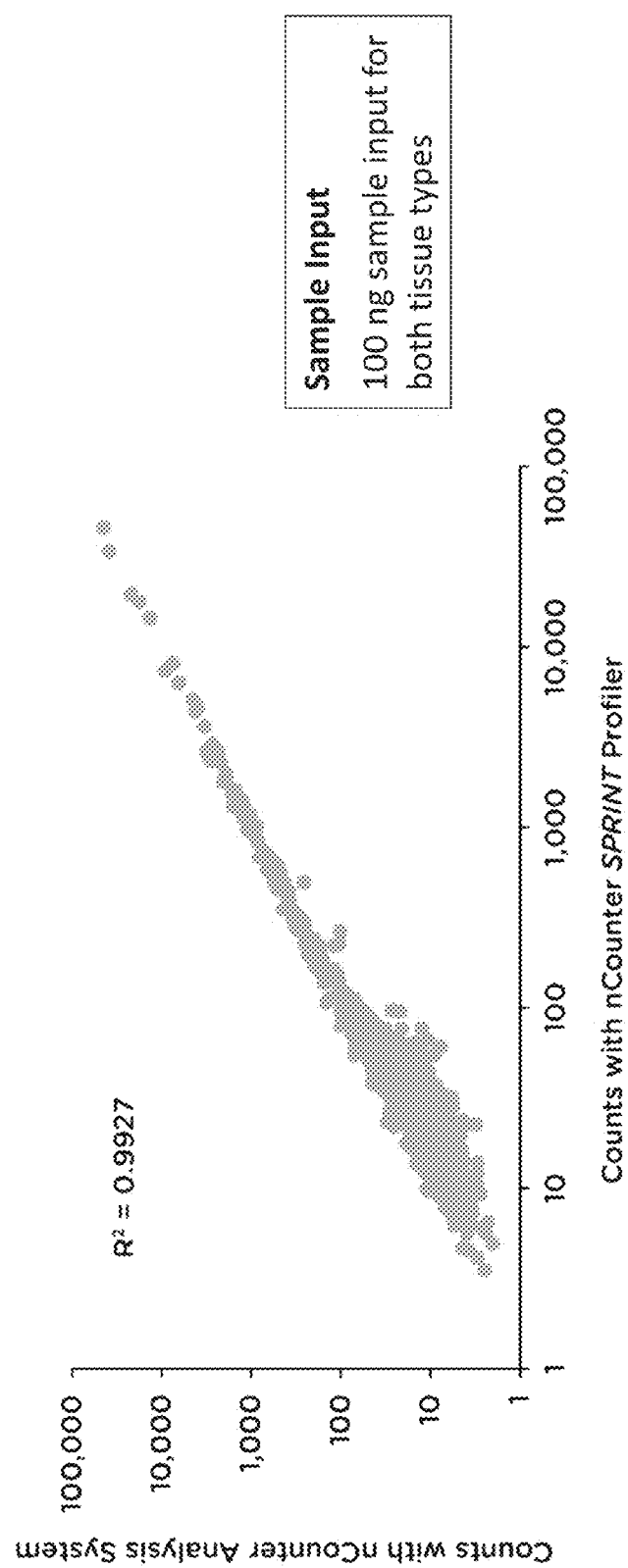
FIG. 29 shows a graph comparing results obtained with the nCounter® Analysis System and results obtained according to some embodiments of the present invention in an a miRNA analysis.
Figure 30:
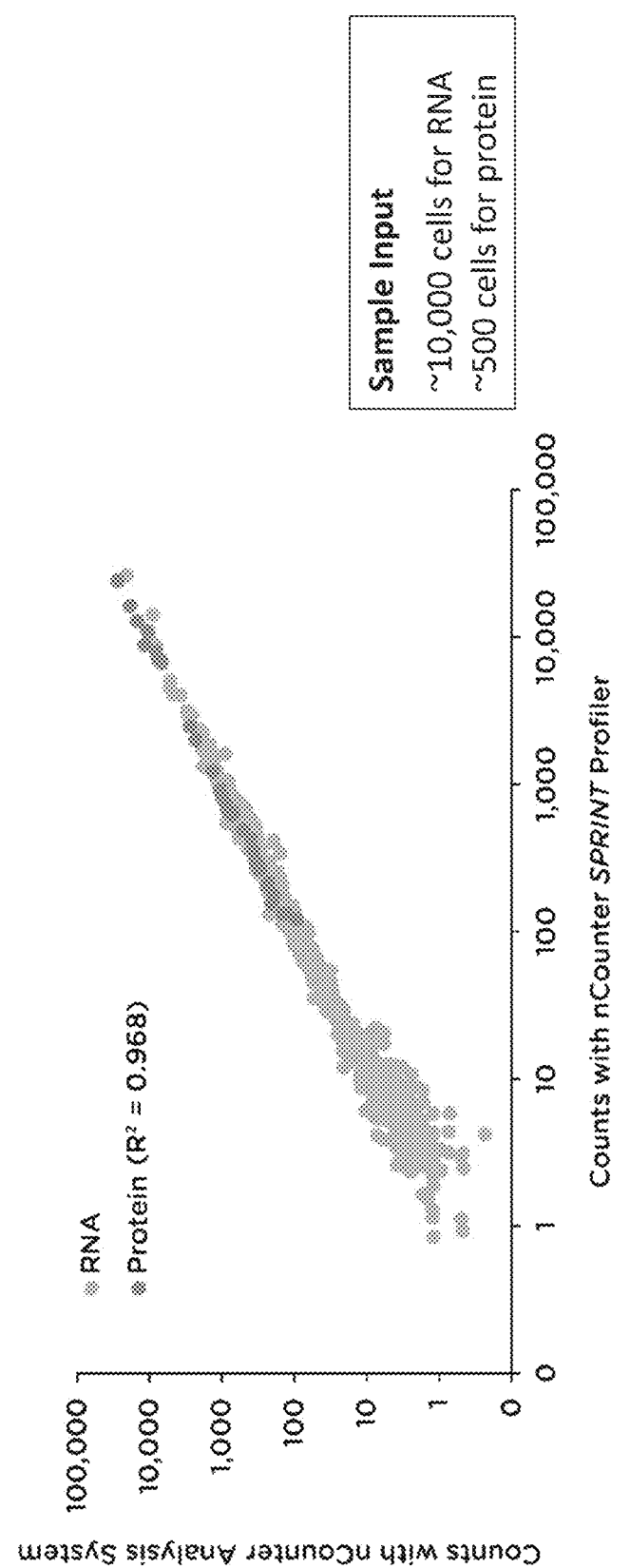
FIG. 30 shows a graph comparing results obtained with the nCounter® Analysis System and results obtained according to some embodiments of the present invention for RNA-Protein Profiling data.

As shown in FIG. 22, embodiments effectively detect targets from three nCounter® PanCancer Panels: the Pan-Cancer Pathways panel, the PanCancer Progression panel, and the PanCancer Immune Profiling panel. Here, data obtained from embodiments (identified in as "nCounter SPRINT Profiler") are correlated with data obtained from the nCounter® Analysis System. As shown in FIG. 23, embodiments enable identification of differentially expressed genes in lymphoma samples. As shown in FIG. 24, embodiments can detect gene expression in purified total RNA or in raw cell lysates; it is notable that assays require limited sample preparation. As shown in FIG. 25, embodiments provide reliable, trustworthy detection of gene expression with various sample types, including, but not limited to, fresh-frozen tissue and Formalin-Fixed Paraffin-Embedded (FFPE) tissues. As shown in FIG. 26, embodiments effectively detect gene expression for the PanCancer Progression Panel and with highly correlated results with respect to results obtained with the nCounter® Analysis System. It is noteworthy that embodiments of the present invention (identified as "SPRINT") used half as much sample input (by weight) as used with the nCounter® Analysis System (identified as "Analysis System"). As shown in FIG. 27, embodiments effectively detect targets in the Human Immunology Panel. Here, data obtained from embodiments (identified as "nCounter SPRINT Profiler") are correlated with data obtained from the nCounter® Analysis System. As shown in FIG. 28, embodiments effectively quantify targets in a copy number variation (CNV) assay. Similar copy number data were obtained for DNA samples run on embodiments of the present invention (identified as "nCounter SPRINT Profiler") and the nCounter® Analysis System. Here, copy number data for each gene is directly above a tick mark on the X-axis. Thus, a vertically-related pair comprising a square (data from embodiments of the present invention) and circle (data from the nCounter® Analysis System) represent data for a particular gene. As shown in FIG. 29, embodiments effectively detect miRNA targets. Here, data obtained from embodiments are correlated with data obtained from the nCounter® Analysis System. As shown in FIG. 30, embodiments effectively detect RNA and protein targets. Here, data obtained from embodiments (identified as "nCounter SPRINT Profiler") are correlated with data obtained from the nCounter® Analysis System.

Any and all references to publications or other documents, including but not limited to, patents, patent applications, articles, webpages, books, etc., presented in the present application, are herein incorporated by reference in their entirety, except insofar as the subject matter may conflict with that of the embodiments of the present disclosure (in which case what is present herein shall prevail). The referenced items are provided solely for their disclosure prior to the filing date of the present application. Nothing herein is to be construed as an admission that any invention disclosed herein is not entitled to antedate such material by virtue of prior invention.

Although example embodiments of the devices, systems and methods have been described herein, other modifications are possible. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. In addition, any logic flow depicted in the above disclosure and/or accompanying figures may not require the particular order shown, or sequential order, to achieve desirable results. Moreover, embodiments of the subject disclosure may include methods, systems and devices which may further include any and all elements from any other disclosed methods, systems, and devices, including any and all elements corresponding to gene purification and imaging. In other words, elements from one and/or another disclosed embodiment may be interchangeable with elements from other disclosed embodiments. In addition, one or more features/elements of disclosed embodiments may be removed and still result in patentable subject matter (and thus, resulting in yet more embodiments of the subject disclosure). In addition, some embodiments of the present disclosure are distinguishable from the prior art for expressly not requiring one and/or another features disclosed in the prior art (e.g., some embodiments may include negative limitations). Some of the embodiments disclosed herein are within the scope of at least some of the following claims of the numerous claims which are supported by the present disclosure which may be presented.

What is claimed is:

1. A cartridge configured for purifying a hybridized target molecule sample and imaging a hybridized target molecule, comprising:
   a sample input area configured to hold a target molecule sample, the sample comprising:
      a plurality of hybridized complexes comprising a plurality of target molecules each hybridized with a first probe and a second probe,
      a plurality of non-hybridized first probes, and
      a plurality of non-hybridized second probes;
   a first binding chamber configured to receive or contain a first affinity matrix and to receive the sample, wherein:
      the first affinity matrix is functionalized with first molecules configured to bind with the non-hybridized first probes and hybridized complexes of the sample during a first period of time;

the first binding chamber is additionally configured to receive a first buffer to remove non-hybridized second probes from the sample after the non-hybridized first probes and hybridized complexes of the sample bind with the first affinity matrix;

a first elution channel attached to the first binding chamber and a means for heating, and which is configured to receive the first affinity matrix after the first period of time and configured for heating the first affinity matrix to elute a first eluted sample comprising the plurality of hybridized complexes and plurality of non-hybridized first probes;

a second binding chamber configured to receive or contain a second affinity matrix and to receive the first eluted sample, wherein:

the second affinity matrix is functionalized with second molecules configured to bind with the hybridized complexes during a second period of time;

the second binding chamber is additionally configured to receive a second buffer to remove at least non-hybridized first probes;

a second elution channel attached to the second binding chamber and a means for heating, and which is configured to receive the second affinity matrix after the second period of time and configured for heating the second affinity matrix to elute a second eluted sample comprising the plurality of hybridized complexes; and a binding area having an active binding surface configured to receive the second eluted sample and bind with the hybridized complexes.

2. The cartridge of claim 1, wherein the target molecule is a nucleic acid or a protein.

3. The cartridge of claim 1, wherein the first affinity matrix and the second affinity matrix correspond to a first set of magnetic beads and a second set of magnetic beads, respectively.

4. The cartridge of claim 1, wherein the active binding surface comprises one of streptavidin, an avidin, and oligonucleotides.

5. The cartridge of claim 3, wherein the cartridge further comprises:
a plurality of buffer input areas,
a plurality of first binding chambers,
a plurality of waste output areas, and
a plurality of bead pads.

6. The cartridge of claim 1, wherein the first probes include capture probes.

7. The cartridge of claim 1, wherein the second probes include reporter probes.

8. The cartridge of claim 5, wherein the bubble vent configured to separate the sample input and the first binding chamber and to eliminate air bubbles.

9. The cartridge of claim 3, wherein the first magnetic beads include oligonucleotide-coupled magnetic beads.

10. The cartridge of claim 9, wherein the oligonucleotide-coupled magnetic beads include F magnetic beads.

11. The cartridge of claim 3, wherein the second magnetic beads include oligonucleotide-coupled magnetic beads.

12. The cartridge of claim 11, wherein the oligonucleotide-coupled magnetic beads include G magnetic beads.

13. The cartridge of claim 1, the cartridge being operatively coupled to:
a plurality of off-card buffer input valves operatively coupled to a fluidic manifold; and
a plurality of waste valves.

14. The cartridge of claim 1, the cartridge further comprising:
a plurality of on-card buffer input valves operatively coupled to a fluidic manifold.

15. The cartridge of claim 13, wherein the plurality of off-card buffer input valves are configured to receive the first buffer and the second buffer from the fluidic manifold and provide the buffer to the cartridge.

16. The cartridge of claim 1, wherein the flow of the second eluted sample onto the binding area is done in small steps that are re-ordered based on pressure profiles.

17. The cartridge of claim 1, wherein the binding area is further configured to receive a solution formulated to immobilize the second eluted sample on the active binding surface after stretching with flow.

18. The cartridge of claim 17, wherein the solution includes G-hooks, anti-fade media, and fiducials.

19. A cartridge configured for purifying a hybridized target molecule sample and imaging the hybridized target molecule, comprising:

a buffer input area configured to hold a target molecule sample, the sample comprising:
a plurality of hybridized complexes including a plurality of target molecules, and each of reporter probes and capture probes,
a plurality of non-hybridized reporter probes, and
a plurality of non-hybridized capture probes;

a bubble vent configured to separate the sample input and the first binding chamber and to eliminate air bubbles;

a first binding chamber configured to receive or contain F magnetic beads and to receive the sample, wherein:

the F magnetic beads are functionalized with first molecules configured to bind with the non-hybridized reporter probes and hybridized complexes of the sample during a first period of time;

the first binding chamber is additionally configured to receive a first buffer to remove non-hybridized reporter probes from the sample after the non-hybridized reporter probes and hybridized complexes of the sample bind with the F magnetic beads;

a first elution channel attached to the first binding chamber and a means for heating, and which is configured to receive the F magnetic beads after the first period of time and configured for heating the F magnetic beads to elute a first eluted sample comprising the plurality of hybridized complexes and plurality of non-hybridized reporter probes;

a second binding chamber configured to receive or contain G magnetic beads and to receive the first eluted sample, wherein:

the G magnetic beads are functionalized with second molecules configured to bind with the hybridized complexes during a second period of time;

the second binding chamber is additionally configured to receive a second buffer remove at least non-hybridized capture probes;

a second elution channel attached to the second binding chamber and a means for heating, and which is configured to receive the G magnetic beads after the second period of time and configured for heating the G magnetic beads to elute a second eluted sample comprising the plurality of hybridized complexes;

a binding area having an active binding surface configured to receive the second eluted sample and bind with the hybridized complexes;

wherein the cartridge is operatively coupled to:

a plurality of off-card buffer input valves operatively coupled to a fluidic manifold, the plurality of off-card buffer input valves being configured to receive the first buffer and the second buffer from the fluidic manifold and provide the first and buffer to the cartridge; and a plurality of waste valves configured to collect the first and second buffer from the cartridge.

20. A system for imaging a plurality of hybridized complexes comprising;

a cartridge according to claim 1;

a cartridge tray operatively coupled to the system and configured to hold the cartridge;

a first heater operatively coupled to the cartridge;

a second heater operatively coupled to the cartridge;

a magnet operatively coupled to the imaging device below the cartridge tray;

a fluidic manifold operatively coupled to the system above the cartridge tray and configured to hold and control the flow of a plurality of buffers;

a plurality of off-card buffer input valves operatively coupled to the fluidic manifold and the cartridge;

a plurality of waste valves operatively coupled to the system above the cartridge tray; and an imaging reference surface operatively coupled to the imaging device above the cartridge tray.

21. A method for purifying a hybridized target molecule sample and imaging the hybridized target molecule, comprising:

providing the cartridge of claim 1;

receiving a hybridized sample, the sample comprising a plurality of hybridized complexes comprising target molecules hybridized with first probes and second probes, a plurality of non-hybridized first probes, and a plurality of non-hybridized second probes;

binding the non-hybridized first probes and hybridized complexes of the sample to a first affinity matrix in a first binding chamber during a first period of time;

flowing a first buffer into the first binding chamber to remove non-hybridized second probes from the sample after the non-hybridized first probes and hybridized complexes of the sample bind with the first affinity matrix;

directing the first affinity matrix into a first elution channel;

heating the first affinity matrix to elute a first eluted sample comprising the plurality of hybridized complexes and plurality of non-hybridized first probes;

binding the hybridized complexes of the first eluted sample to a second affinity matrix in a second binding chamber during a second period of time;

flowing a second buffer into the second binding chamber to remove the non-hybridized first probes from the first eluted sample after the hybridized complexes bind with the second affinity matrix;

heating the second affinity matrix to elute a second eluted sample comprising the plurality of hybridized complexes; and binding the hybridized complexes to an active binding surface for imaging thereof.

* * * * *